(12) United States Patent
Marti et al.

(10) Patent No.: US 11,618,887 B2
(45) Date of Patent: Apr. 4, 2023

(54) METHOD AND APPARATUS FOR MESENCHYMAL STEM CELLS PURIFICATION

(71) Applicant: Guy Marti, Montigny-sur-Loing (FR)

(72) Inventors: Guy Marti, Montigny-sur-Loing (FR); Frank Lay, Baltimore, MD (US); John W. Harmon, Baltimore, MD (US); Louis Joseph Born, Pasadena, MD (US); Zahra Alikhassy Habibabady, Baltimore, MD (US); Aurelien Markus Marti, Moret-Loing-et-Orvanne (FR)

( * ) Notice: Subject to any disclaimer, the term of this patent is extended or adjusted under 35 U.S.C. 154(b) by 354 days.

(21) Appl. No.: 16/759,008

(22) PCT Filed: Oct. 26, 2018

(86) PCT No.: PCT/EP2018/079504
§ 371 (c)(1),
(2) Date: Apr. 24, 2020

(87) PCT Pub. No.: WO2019/081765
PCT Pub. Date: May 2, 2019

(65) Prior Publication Data
US 2021/0180025 A1 Jun. 17, 2021

Related U.S. Application Data

(60) Provisional application No. 62/577,269, filed on Oct. 26, 2017.

(51) Int. Cl.
*C12N 5/0775* (2010.01)
*C12M 1/00* (2006.01)
(52) U.S. Cl.
CPC .......... *C12N 5/0667* (2013.01); *C12M 45/05* (2013.01)
(58) Field of Classification Search
None
See application file for complete search history.

(56) References Cited

U.S. PATENT DOCUMENTS 4,242,460 A 12/1980 Chick et al.

FOREIGN PATENT DOCUMENTS

WO 2011/069117 A1 6/2011

OTHER PUBLICATIONS

Geng et al. "Fabrication of Reusable Whole PDMS Biochip for Mesenchymal Stem Cell Seperation and Enrichment" (2011), Proceedings of the 2011 6th IEEE Conf. on Nano/Micro Engineered and Molecular systems. (Year: 2011).*
Lee et al. "High-throughput cell cycle synchronization using inertial forces in spiral microchannels" (2011), Lab Chip, vol. 11: 1359-1367. (Year: 2011).*
International Search Report issued on Jan. 16, 2019 in corresponding International Application No. PCT/EP2018/079504; 5 pages.
Hongjun Song et al., "Continuous-flow sorting of stem cells and differentiation products based on dielectrophoresis", Lab on a Chip, vol. 15, No. 5, Jan. 1, 2015, pp. 1320-1328.
Lorenz Meinel et al., "Bone Tissue Engineering Using Human Mesenchymal Stem Cells: Effects of Scaffold Material and Medium Flow", Annals of Biomedical Engineering, Springer US, New York, vol. 32, No. 1, Jan. 1, 2004, pp. 112-122.
Leandra S. Baptista et al., "An alternative method for the isolation of mesenchymal stromal cells derived from lipoaspirate samples", Cytotherapy, 2019, vol. 11, No. 6, pp. 706-715.
Joris A. Van Dongen et al., "The fractionation of adipose tissue procedure to obtain stromal vascular fractions for regenerative purposes", Wound Repair and Regeneration, 2016, vol. 24, pp. 994-1003.

\* cited by examiner

*Primary Examiner* — Teresa E Knight
(74) *Attorney, Agent, or Firm* — Maier & Maier, PLLC

(57) ABSTRACT

A method of purifying adipose-derived mesenchymal stem cells from a sample of adipose tissue, including: flowing the sample onto a polymer surface having at least one vertical helical-shaped portion, vertical threaded shaped portion, or vertical grooved shaped portion at a first flow rate of 10 to 150 ml/min allowing separation into a first remaining sample including mesenchymal stem cells on the polymer surface and into a second resulting solution being evacuated from the polymer surface; flowing a saline solution onto the polymer surface at a second flow rate of 100 to 500 ml/min, the first flow rate being slower than the second flow rate; and collecting the saline solution including purified mesenchymal stem cells in a collector. Also, an apparatus and a system for purifying adipose-derived mesenchymal stem cells, the use of the apparatus, and a method of isolating and purifying adipose-derived mesenchymal stem cells from an adipose tissue sample.

15 Claims, 7 Drawing Sheets

METHOD AND APPARATUS FOR MESENCHYMAL STEM CELLS PURIFICATION

FIELD

The present invention pertains to the field of stem cells purification. In particular, the invention relates to methods and apparatuses for mesenchymal stem cells purification. Another object relates to mesenchymal stem cells isolation and purification, especially for subsequent therapeutic applications.

BACKGROUND

Initially, mesenchymal stem cells isolation and purification proposed in the 1960s comprised together washing, heat treatment, chemical treatment by use of enzymes and centrifugation rounds.

However, the use of enzymes, such as collagenase and trypsin, is not recommended on stem cells as it may significantly modify the cells. Furthermore, clinical grade collagenase is expensive.

Consequently, non-enzymatic methods for isolation of mesenchymal stem cells have been developed.

For instance, Van Dongen et al. discloses a procedure to isolate stromal vascular fractions comprising mesenchymal stem cells from condensed lipoaspirate. The fractionation comprises a centrifugation round and then mechanical dissociation. The mechanical dissociation comprises two syringes and a Luer to Luer connector with three 1.4 mm holes. The condensed lipoaspirate is pushed through the Luer to Luer connector forward and backwards thirty times. Said process enables to obtain the stromal vascular fraction from adipose tissue in a sparing way, which is directly available for therapeutic injection. However, the stromal vascular fraction does not comprise purified mesenchymal stem cells but also the extracellular matrix and the microvasculature. In order to purify the stromal vascular fraction Van Dongen et al. proposed anew the digestion with enzymes (namely, collagenase), a centrifugation round and the plating in a culture ware (Van Dongen et al., Wound Repair and Regeneration, Vol. 24, pages 994-1003, 2016).

Baptista et al. concerns the isolation of mesenchymal stem cells by use of two centrifugation steps and subsequent plating in culture dishes for up to 2 weeks. The mesenchymal stem cells are isolated by washing based on their adherence properties on the plastic culture dishes after 2 weeks (Baptista et al., Cryotherapy, Vol. 11, No 6, pages 706-715, 2009). Adhesion-based collection and separation of cells as described by Baptista et al requires time (up to 2 weeks) during which stem cells may start to differentiate.

Having regard to the state of the art identified above, one of the object underlying the present invention is to provide a non-enzymatic mechanical method of purifying mesenchymal stem cells. Another object of the present invention is to provide a simple and fast method therefore.

To that end, the present invention provides a method of purifying mesenchymal stem cells based on the partitioning of stem cells from other components due to their flow rate on a polymer surface.

In view of the fastness of the method of the invention, the purified stem cells may advantageously be isolated from one patient and reintroduced to said patient during the same surgical procedure.

SUMMARY

The present invention relates to a method of purifying adipose-derived mesenchymal stem cells from a sample of adipose tissue comprising mesenchymal stem cells, comprising the steps of:
 optionally mixing said sample using a vortex mixer;
 flowing said sample comprising mesenchymal stem cells on a polymer surface, preferably a polystyrene surface, at a first flow rate allowing to separating said sample into a first remaining sample comprising mesenchymal stem cells on the polymer surface and into a second resulting solution being evacuated from the polymer surface;
 flowing a saline solution on said polymer surface at a second flow rate different from the first flow rate; and
 collecting the saline solution comprising purified mesenchymal stem cells in a collector;
 wherein the first flow rate is slower than the second flow rate;
 wherein the first flow rate is ranging from 10 to 150 ml/min;
 wherein the second flow rate is ranging from 100 to 500 ml/min; and
 wherein the polymer surface comprises at least one vertical helical-shaped portion, at least one vertical threaded shaped portion, or at least one vertical grooved shaped portion.

In one embodiment, the ratio between the first flow rate and the second flow rate is ranging from 2 to 50.

In one embodiment, the polymer surface is the inner surface of a pipe, a tube, a conduit, a duct, a gutter, an open-pipe, or a channel.

In one embodiment, a portion of the pipe has at least one dimension ranging from 1 mm to 1 cm.

The present invention also relates an apparatus for purifying adipose-derived mesenchymal stem cells, comprising a polymer surface, preferably a polystyrene surface, wherein the polymer surface comprises a geometrical design inducting a minimal flow rate when a control solution is introduced into said polymer surface; wherein the polymer surface comprises at least one vertical helical-shaped portion, at least one vertical threaded shaped portion, or at least one vertical grooved shaped portion.

In one embodiment, the apparatus further comprises a lumen extending between at least one inlet and at least one outlet, wherein the lumen comprises at least one portion of a polymer surface.

In one embodiment, the polymer surface extends between at least one inlet and at least one outlet, comprises a portion having at least one dimension ranging from 1 mm to 1 cm, and is the surface of a three-dimensional system configured such that as a sample moves forward on said polymer surface, the gravitational potential energy of said sample decreases on at least a portion of said polymer surface.

The present invention also relates to the use of the apparatus of the invention for purifying adipose-derived mesenchymal stem cells.

The present invention also relates to a system for purification of adipose-derived mesenchymal stem cells, comprising:
 an apparatus of the invention;
 at least one supplier fluidly connected to the at least one inlet of the apparatus and configured to be fluidly connected to at least one reservoir comprising at least one sample comprising mesenchymal stem cells and to at least one reservoir comprising at least one saline solution;

at least one collector fluidly connected to the at least one outlet of the apparatus;

at least one flow controller configured to control the flow rate of a fluid passing through the supplier either at a first flow rate or at a second flow rate; and optionally a flowcytometer;

wherein the first flow rate is slower than the second flow rate;

wherein the first flow rate is ranging from 10 to 150 ml/min; and wherein the second flow rate is ranging from 100 to 500 ml/min.

In one embodiment, the apparatus comprises two inlets and the supplier comprises two tubing; a first tubing configured to fluidly connect the first inlet to at least one sample comprising mesenchymal stem cells and the second tubing configured to fluidly connect the second inlet to at least one saline solution, and wherein the flow controller are configured to flow a fluid passing through the first tubing at a first flow rate and to flow a fluid passing through the second tubing at a second flow rate, wherein the first flow rate is slower than the second flow rate.

The present invention also related to a method of isolating and purifying adipose-derived mesenchymal stem cells from a sample of adipose tissue, comprising the steps of:

optionally mixing said sample using a vortex mixer;

subjecting the sample to at least one centrifugation round;

collecting the centrifuged layer comprising mesenchymal stem cells;

flowing said layer comprising mesenchymal stem cells on a polymer surface, preferably a polystyrene surface, at a first flow rate allowing to separate said sample into a first remaining sample comprising mesenchymal stem cells on the polymer surface and into a second resulting solution being evacuated from the polymer surface;

flowing a saline solution on said polymer surface at a second flow rate; and collecting the saline solution comprising purified mesenchymal stem cells in a collector;

wherein the first flow rate is slower than the second flow rate;

wherein the first flow rate is ranging from 10 to 150 ml/min;

wherein the second flow rate is ranging from 100 to 500 ml/min; and wherein the polymer surface (1) comprises at least one vertical helical-shaped portion, at least one vertical threaded shaped portion, or at least one vertical grooved shaped portion.

In one embodiment, the step of subjecting the sample to at least one centrifugation round comprises the steps of:

subjecting the sample comprising adipose tissue to a first centrifugation round;

collecting the intermediate centrifuged layer;

subjecting said intermediate centrifuged layer to a second centrifugation round; and collecting the superficial centrifuged layer comprising mesenchymal stem cells.

DETAILED DESCRIPTION

In the present invention, the following terms have the following meanings:

"Purification" refers herein to the preparation of a pure population of one type of cells. A suspension of stem cells is referred to as purified if it is free of cellular debris or extracellular matrix product.

"Isolation" refers to the extraction of cells from their original environment. A suspension of stem cells is referred to as isolated if it is free of pre-adipocytes, endothelial cells, smooth muscle cells, pericytes, fibroblasts, erythrocytes, B and T cells, macrophages, monocytes or mast cells.

"Mesenchymal stem cells" refers to multipotent stromal cells that can differentiate into a variety of cell types. In mammals, they are found in multicellular bone marrow, adipose tissue (referred to as adipose-derived mesenchymal stem cells) or blood. "Mesenchymal stem cells" are not human embryonic stem cells (hESC) obtained by a method resulting in the destruction of the embryo. "Mesenchymal stem cells" may also refer to blood umbilical cord stem cells, molar stem cells, amniotic fluid stem cells, follicular stem cells, or human embryonic stem cells (hESC) obtained without the destruction of an embryo using a method such as for example the one described in Chung et al., Cell Stem Cell, Vol. 2 (2), pages 113-117, 2008.

"Spiral pipe" refers to a three-dimensional helical pipe member that turns around a helical axis (AB) at a constant or continuously varying distance and/or width.

"Automated", "Semi-automated" and "Manual" refer to operating methods. "Automated" refers to an operating method, wherein all the steps are independent of external control. "Semi-automated" refers to an operating method, wherein at least one step is automated and at least one step is manual. "Manual" refers to an operating method, wherein all the steps are operated by hand.

"Saline solution" refers to a mixture of sodium chloride in water.

"Microfluidic" refers to a structure comprising at least one channel having at least one dimension ranging from 1 to 100 nm.

The following detailed description will be better understood when read in conjunction with the drawings. For the purpose of illustrating, the apparatus is shown in the preferred embodiments. It should be understood, however that the application is not limited to the precise arrangements, structures, features, embodiments, and aspect shown. The drawings are not drawn to scale and are not intended to limit the scope of the claims to the embodiments depicted. Accordingly, it should be understood that where features mentioned in the appended claims are followed by reference signs, such signs are included solely for the purpose of enhancing the intelligibility of the claims and are in no way limiting on the scope of the claims.

Figure 1:
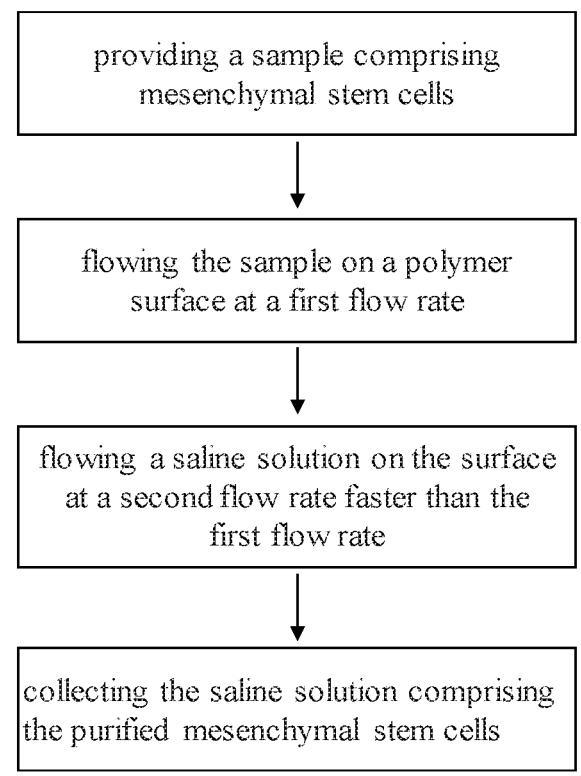
FIG. 1 is a histogram showing the method of purifying adipose-derived mesenchymal stem cells according to the invention.
Figure 2:
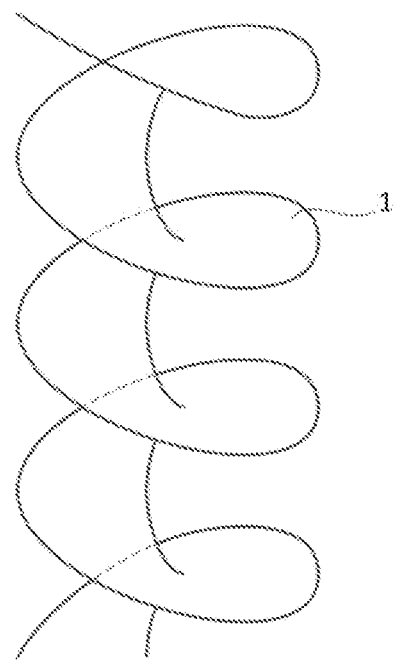
FIG. 2 illustrates a polymer surface 1 according to an embodiment of the invention.

In a first aspect, illustrated in FIGS. 1 and 2, this invention relates to a method of purifying adipose-derived mesenchymal stem cells from a sample of adipose tissue comprising mesenchymal stem cells, comprising the steps of:

flowing said sample comprising mesenchymal stem cells on a polymer surface 1, preferably a polystyrene surface, at a first flow rate allowing to separate said sample into a first remaining sample comprising mesenchymal stem cells on the polymer surface 1 and into a second resulting solution being evacuated from the polymer surface 1;

flowing a saline solution on said polymer surface 1 at a second flow rate different from the first flow rate; and collecting the saline solution comprising purified mesenchymal stem cells in a collector.

The first flow rate is slower than the second flow rate. The first flow rate is ranging from 10 to 150 ml/min. The second flow rate is ranging from 100 to 500 ml/min.

Said method is based on the adherence properties of mesenchymal stem cells on polymer materials. By flowing on a polymer surface 1, the mesenchymal stem cells decelerate while other cells and particles are carried away allowing to separate the sample into a first remaining sample comprising mesenchymal stem cells on the polymer surface 1 and into a second resulting solution being evacuated from the polymer surface 1.

The polymer surface 1 must revolve around a vertical axis (AB), preferably a vertical helix, enabling the gravity to push the sample comprising the stem cells along said polymer surface 1. The contribution of gravity to the method is compulsory for a good separation of mesenchymal stem cells from the sample. The gravity of the sample will allow enough time for the stem cells to reach contact with the polymer surface and be attracted to it. Indeed, mesenchymal cells being small cells and a rapid flow would carry them away quickly without allowing time for contact with the polymer surface.

The polymer surface is not a planar surface, i.e. is not comprised in a geometrical plane, and does not comprise a planar portion. Indeed, a planar surface would not allow the gravity to act on the sample and would not result in a good separation of the mesenchymal stem cells from said sample.

According to the Applicant, by advantageously selecting the first flow rate, the material of the surface of said surface, the mesenchymal stem cells do not adhere on the surface but only slow down due to their natural attraction to the surface. Thus, stem cells are retained due to their attraction to the polymer surface 1 while other components of the first flow (cellular debris, extracellular matrix product, pre-adipocytes . . . ) are drained away at a rate equal to the first flow rate. However, it is important that the mesenchymal stem cells do not adhere on the polymer surface 1 so that they are not attached to said polymer surface 1 to prevent the risk of differentiation of the stem cells. The length of the polymer surface 1 may also be of importance as the longer the surface is, the more the stem cells may be retained.

The purified mesenchymal stem cells may be delivered immediately to different specialists for the treatment of a variety of conditions, for instance in orthopedics (joint diseases, bone grafts), ophthalmology (macular degeneration, glaucoma), uro-gynecology (urinary incontinence, erectile dysfunction), plastic surgery (face peels, hair regrowth, scars, lipofilling, lipostructure, breast augmentation), wound healing, salivary glands stimulation after radiotherapy, peripheral arterial disease. The purified mesenchymal stem cells may be reinjected in the subject that provided the sample of adipose tissue. They may be injected in joints, salivary glands, retina, skin, muscle, or mixed with bone graft. These cells may be used for any tissue regeneration procedure or method. They may also be topically applied on wounds, burn wounds, ulcers, after chemical or mechanical face peeling.

The saline solution comprising purified mesenchymal stem cells is also referred hereafter as a suspension of purified mesenchymal stem cells.

In one embodiment, the method further comprises step of mixing the sample using a vortex mixer before flowing the sample comprising mesenchymal stem cells on a polymer surface 1.

In one embodiment, the method is chemical-free and enzyme-free. In this embodiment, the method is compliant with the requirements of Regulation (EC) no 1394/2007 of the European Parliament and of the Council of 13 Nov. 2007 on advanced therapy medicinal products. This embodiment prevents a chemical modification or pollution of the stem cells.

In one embodiment, the method is performed in less than 15 minutes. This method is very fast and allows the use the purified stem cells in clinical application in situ: the sample of adipose tissue can be provided and the resulting stem cells can be purified during the same clinical procedure.

In one embodiment, the method is performed in less than 15 minutes, 10 minutes, or 5 minutes.

In one embodiment, the method of present invention is manual.

In one embodiment, the method of present invention is semi-automated.

In one embodiment, the method of present invention is automated.

In one embodiment, the mesenchymal stem cells are adipose-derived mesenchymal stem cells. In said embodiment, the sample is preferably a sample of adipose tissue.

In one embodiment, the mesenchymal stem cells are bone marrow-derived mesenchymal stem cells.

In one embodiment, the mesenchymal stem cells are blood-derived mesenchymal stem cells.

In one embodiment, the mesenchymal stem cells are blood umbilical cord stem cells, molar stem cells, amniotic fluid stem cells, follicular stem cells, or human embryonic stem cells (hESC) obtained without the destruction of an embryo using a method such as for example the one described in Chung et al., Cell Stem Cell, Vol. 2 (2), pages 113-117, 2008.

In one embodiment, the method of the invention is used to purify mesenchymal stem cells such as for example blood umbilical cord stem cells, molar stem cells, amniotic fluid stem cells, follicular stem cells, or human embryonic stem cells (hESC) obtained without the destruction of an embryo using a method such as for example the one described in Chung et al., Cell Stem Cell, Vol. 2 (2), pages 113-117, 2008.

In one embodiment, the mesenchymal stem cells do not differentiate during the method.

In one embodiment, the sample is a lipoaspirate.

In one embodiment, the method further comprises a step of providing a sample comprising adipose tissue. In this embodiment, the sample is provided prior flowing said sample on a polymer surface 1.

In one embodiment, the sample of adipose tissue is obtained by a minimally invasive procedure such as lipoaspiration, or minimally invasive surgery. In this embodiment, surgery may comprise incision and dissection.

In one embodiment, the sample of adipose tissue is obtained by any means known by the person skilled in the art.

In one embodiment, the sample has a volume ranging from 20 cm$^3$ to 200 cm$^3$.

In one embodiment, the sample has a volume of at least 20 cm$^3$, 30 cm$^3$, 40 cm$^3$, 50 cm$^3$, 60 cm$^3$, 70 cm$^3$, 80 cm$^3$, 90 cm$^3$, 100 cm$^3$, 110 cm$^3$, 120 cm$^3$, 130 cm$^3$, 140 cm$^3$, 150 cm$^3$, 160 cm$^3$, 170 cm$^3$, 180 cm$^3$, 190 cm$^3$, or 200 cm$^3$.

In one embodiment, the sample has a volume ranging from $20 \times 10^{-6}$ m$^3$ to $200 \times 10^{-6}$ m$^3$.

In one embodiment, the sample comprises unpurified mesenchymal stem cells. In this embodiment, the sample may comprise mesenchymal stem cells, cellular debris, extracellular matrix product, pre-adipocytes, leucocytes, endothelial cells, smooth muscle cells, pericytes, fibroblasts, erythrocytes, B and T cells, macrophages, monocytes, or mast cells.

In one embodiment, the first flow rate is at least 10 ml/min, 11 ml/min, 12 ml/min, 13 ml/min, 14 ml/min, 15 ml/min, 16 ml/min, 17 ml/min, 18 ml/min, 19 ml/min, 20 ml/min, 21 ml/min, 22 ml/min, 23 ml/min, 24 ml/min, 25 ml/min, 26 ml/min, 27 ml/min, 28 ml/min, 29 ml/min, 30 ml/min, 31 ml/min, 32 ml/min, 33 ml/min, 34 ml/min, 35 ml/min, 36 ml/min, 37 ml/min, 38 ml/min, 39 ml/min, 40 ml/min, 41 ml/min, 42 ml/min, 43 ml/min, 44 ml/min, 45 ml/min, 46 ml/min, 47 ml/min, 48 ml/min, 49 ml/min, 50 ml/min, 51 ml/min, 52 ml/min, 53 ml/min, 54 ml/min, 55 ml/min, 56 ml/min, 57 ml/min, 58 ml/min, 59 ml/min, 60 ml/min, 61 ml/min, 62 ml/min, 63 ml/min, 64 ml/min, 65 ml/min, 66 ml/min, 67 ml/min, 68 ml/min, 69 ml/min, 70 ml/min, 71 ml/min, 72 ml/min, 73 ml/min, 74 ml/min, 75 ml/min, 76 ml/min, 77 ml/min, 78 ml/min, 79 ml/min, 80 ml/min, 81 ml/min, 82 ml/min, 83 ml/min, 84 ml/min, 85 ml/min, 86 ml/min, 87 ml/min, 88 ml/min, 89 ml/min, 90 ml/min, 91 ml/min, 92 ml/min, 93 ml/min, 94 ml/min, 95 ml/min, 96 ml/min, 97 ml/min, 98 ml/min, 99 ml/min, 100 ml/min, 110 ml/min, 120 ml/min, 130 ml/min, 140 ml/min, or 150 ml/min.

In one embodiment, the second flow rate is at least 100 ml/min, 110 ml/min, 120 ml/min, 130 ml/min, 140 ml/min, 150 ml/min, 160 ml/min, 170 ml/min, 180 ml/min, 190 ml/min, 200 ml/min, 210 ml/min, 220 ml/min, 230 ml/min, 240 ml/min, 250 ml/min, 260 ml/min, 270 ml/min, 280 ml/min, 290 ml/min, 300 ml/min, 310 ml/min, 320 ml/min, 330 ml/min, 340 ml/min, 350 ml/min, 360 ml/min, 370 ml/min, 380 ml/min, 390 ml/min, 400 ml/min, 410 ml/min, 420 ml/min, 430 ml/min, 440 ml/min, 450 ml/min, 460 ml/min, 470 ml/min, 480 ml/min, 490 ml/min, or 500 ml/min.

In one embodiment, the ratio between the first flow rate and the second flow rate is ranging from 2 to 50.

In one embodiment, the ratio between the first flow rate and the second flow rate is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

In one embodiment, the first flow rate is configured to be fast enough so that the mesenchymal stem cells do not adhere to the polymer surface 1, and slow enough so that said mesenchymal stem cells decelerate in the vicinity of the polymer surface 1. In this embodiment, the mesenchymal stem cells decelerate when flowing on the polymer surface 1 while other cells or cellular debris are carried away with said flow. Thus, said mesenchymal stem cells are retained for a short time on the polymer surface 1, this time being short enough to prevent the differentiation of the stem cells. The differentiated flow of the mesenchymal stem cells compared to other cells or cellular debris comprised in the sample allows for the purification of said mesenchymal stem cells.

In one embodiment, a sample comprising mesenchymal stem cells is flowed on the polymer surface 1; and/or a saline solution is flowed on the polymer surface 1. In this embodiment, "flowed" means using the gravity to push the sample and saline solution along the polymer surface 1.

In one embodiment, the saline solution comprises NaCl in water at a level ranging from 0.20 to 0.90% w/v.

In one embodiment, the saline solution comprises NaCl in water at a level ranging from 0.20 to 0.90‰.

In one embodiment, the saline solution comprises 0.90% w/v of NaCl in water.

In one embodiment, the saline solution comprises 0.90‰ of NaCl in water.

In one embodiment, the saline solution comprises 0.45% w/v of NaCl in water.

In one embodiment, the saline solution comprises 0.45‰ of NaCl in water.

In one embodiment, the second flow rate is configured to be faster than the first flow rate, and fast enough so that the mesenchymal stem cells are carried away with said second flow.

In one embodiment, the purified mesenchymal stem cells are collected with a container, a pipette, by gently scrubbing the polymer surface 1 and/or by gently agitating the polymer surface 1.

In one embodiment, the purified mesenchymal stem cells may comprise leucocytes. Indeed, treatment of certain infections or for a use under a scar does not require a lack of leucocytes in the mesenchymal stem cells used.

In one embodiment, the purified mesenchymal stem cells may comprise leucocytes at a level ranging from 1 to 1000% of the total purified mesenchymal stem cells volume.

In one embodiment, the purified mesenchymal stem cells do not comprise leucocytes. This embodiment is especially advantageous for knee, hip joint, or eye treatment.

In one embodiment, the purified mesenchymal stem cells do not comprise cellular debris, extracellular matrix product, pre-adipocytes, leucocytes, endothelial cells, smooth muscle cells, pericytes, fibroblasts, erythrocytes, B and T cells, macrophages, monocytes, or mast cells. Cellular debris could indeed trigger an inflammatory reaction. This embodiment allows the injection of said purified mesenchymal stem cells in a subject.

In one embodiment, the purified mesenchymal stem cells are ready to be used.

In one embodiment, the material of the polymer surface 1 is polystyrene. The mesenchymal stem cells are known to have adherent properties on polystyrene.

In one embodiment, the material of the polymer surface 1 is 100% polystyrene, i.e. pure polystyrene.

In one embodiment, the polymer surface 1 is modified using high voltage corona or plasma surface activation to increase the adhesive properties of the mesenchymal stem cells on said polymer surface 1.

In one embodiment, the polymer surface 1 is not functionalized. In this embodiment, the polymer surface 1 is not subjected to any surface treatment, and is not coated with a material that could detach and pollute the mesenchymal stem cells.

In one embodiment, the polymer surface 1 is sterile.

In one embodiment, the polymer surface 1 has a length ranging from 10 cm to 100 cm.

In one embodiment, the polymer surface 1 has a length of at least 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, 25 cm, 26 cm, 27 cm, 28 cm, 29 cm, 30 cm, 31 cm, 32 cm, 33 cm, 34 cm, 35 cm, 36 cm, 37 cm, 38 cm, 39 cm, 40 cm, 41 cm, 42 cm, 43 cm, 44 cm, 45 cm, 46 cm, 47 cm, 48 cm, 49 cm, 50 cm, 51 cm, 52 cm, 53 cm, 54 cm, 55 cm, 56 cm, 57 cm, 58 cm, 59 cm, 60 cm, 61 cm, 62 cm, 63 cm, 64 cm, 65 cm, 66 cm, 67 cm, 68 cm, 69 cm, 70 cm, 71 cm, 72 cm, 73 cm, 74 cm, 75 cm, 76 cm, 77 cm, 78 cm, 79 cm, 80 cm, 81 cm, 82 cm, 83 cm, 84 cm, 85 cm, 86 cm, 87 cm, 88 cm, 89 cm, 90 cm, 91 cm, 92 cm, 93 cm, 94 cm, 95 cm, 96 cm, 97 cm, 98 cm, 99 cm, or 100 cm.

In one embodiment, the polymer surface 1 has a length ranging from $10 \times 10^{-2}$ m to 1 m.

In one embodiment, the polymer surface 1 comprises a portion having at least one dimension ranging from 1 mm to 1 cm. Said dimension may refer to the width, the section, the diameter or any other dimension of the polymer surface 1.

In one embodiment, the polymer surface 1 comprises a portion of at least one dimension of at least 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, 6.1 mm, 6.2 mm, 6.3 mm, 6.4 mm, 6.5 mm, 6.6 mm, 6.7 mm, 6.8 mm, 6.9 mm, 7 mm, 7.1 mm, 7.2 mm, 7.3 mm, 7.4 mm, 7.5 mm, 7.6 mm, 7.7 mm, 7.8 mm, 7.9 mm, 8 mm, 8.1 mm, 8.2 mm, 8.3 mm, 8.4 mm, 8.5 mm, 8.6 mm, 8.7 mm, 8.8 mm, 8.9 mm, 9 mm, 9.1 mm, 9.2 mm, 9.3 mm, 9.4 mm, 9.5 mm, 9.6 mm, 9.7 mm, 9.8 mm, 9.9 mm, or 1 cm.

In one embodiment, the polymer surface 1 comprises a portion having at least one dimension ranging from $1 \times 10^{-3}$ m to $1 \times 10^{-2}$ m. Said dimension may refer to the width, the section, the diameter or any other dimension of the polymer surface.

In one embodiment, the section of the polymer surface 1 ranges from 1 $mm^2$ to 1 $cm^2$.

In one embodiment, the section of the polymer surface 1 is at least 1 $mm^2$, 1.1 $mm^2$, 1.2 $mm^2$, 1.3 $mm^2$, 1.4 $mm^2$, 1.5 $mm^2$, 1.6 $mm^2$, 1.7 $mm^2$, 1.8 $mm^2$, 1.9 $mm^2$, 2 $mm^2$, 2.1 $mm^2$, 2.2 $mm^2$, 2.3 $mm^2$, 2.4 $mm^2$, 2.5 $mm^2$, 2.6 $mm^2$, 2.7 $mm^2$, 2.8 $mm^2$, 2.9 $mm^2$, 3 $mm^2$, 3.1 $mm^2$, 3.2 $mm^2$, 3.3 $mm^2$, 3.4 $mm^2$, 3.5 $mm^2$, 3.6 $mm^2$, 3.7 $mm^2$, 3.8 $mm^2$, 3.9 $mm^2$, 4 $mm^2$, 4.1 $mm^2$, 4.2 $mm^2$, 4.3 $mm^2$, 4.4 $mm^2$, 4.5 $mm^2$, 4.6 $mm^2$, 4.7 $mm^2$, 4.8 $mm^2$, 4.9 $mm^2$, 5 $mm^2$, 5.1 $mm^2$, 5.2 $mm^2$, 5.3 $mm^2$, 5.4 $mm^2$, 5.5 $mm^2$, 5.6 $mm^2$, 5.7 $mm^2$, 5.8 $mm^2$, 5.9 $mm^2$, 6 $mm^2$, 6.1 $mm^2$, 6.2 $mm^2$, 6.3 $mm^2$, 6.4 $mm^2$, 6.5 $mm^2$, 6.6 $mm^2$, 6.7 $mm^2$, 6.8 $mm^2$, 6.9 $mm^2$, 7 $mm^2$, 7.1 $mm^2$, 7.2 $mm^2$, 7.3 $mm^2$, 7.4 $mm^2$, 7.5 $mm^2$, 7.6 $mm^2$, 7.7 $mm^2$, 7.8 $mm^2$, 7.9 $mm^2$, 8 $mm^2$, 8.1 $mm^2$, 8.2 $mm^2$, 8.3 $mm^2$, 8.4 $mm^2$, 8.5 $mm^2$, 8.6 $mm^2$, 8.7 $mm^2$, 8.8 $mm^2$, 8.9 $mm^2$, 9 $mm^2$, 9.1 $mm^2$, 9.2 $mm^2$, 9.3 $mm^2$, 9.4 $mm^2$, 9.5 $mm^2$, 9.6 $mm^2$, 9.7 $mm^2$, 9.8 $mm^2$, 9.9 $mm^2$, or 1 $cm^2$.

In one embodiment, the section of the polymer surface 1 ranges from $1 \times 10^{-6}$ $m^2$ to $1 \times 10^{-4}$ $m^2$.

In one embodiment, the polymer surface 1 is not a microfluidic structure.

In one embodiment, the polymer surface 1 does not comprise any protrusion or depression.

In one embodiment, the polymer surface 1 comprises at least one protrusion.

In one embodiment, the polymer surface 1 comprises at least one depression.

Figure 3:
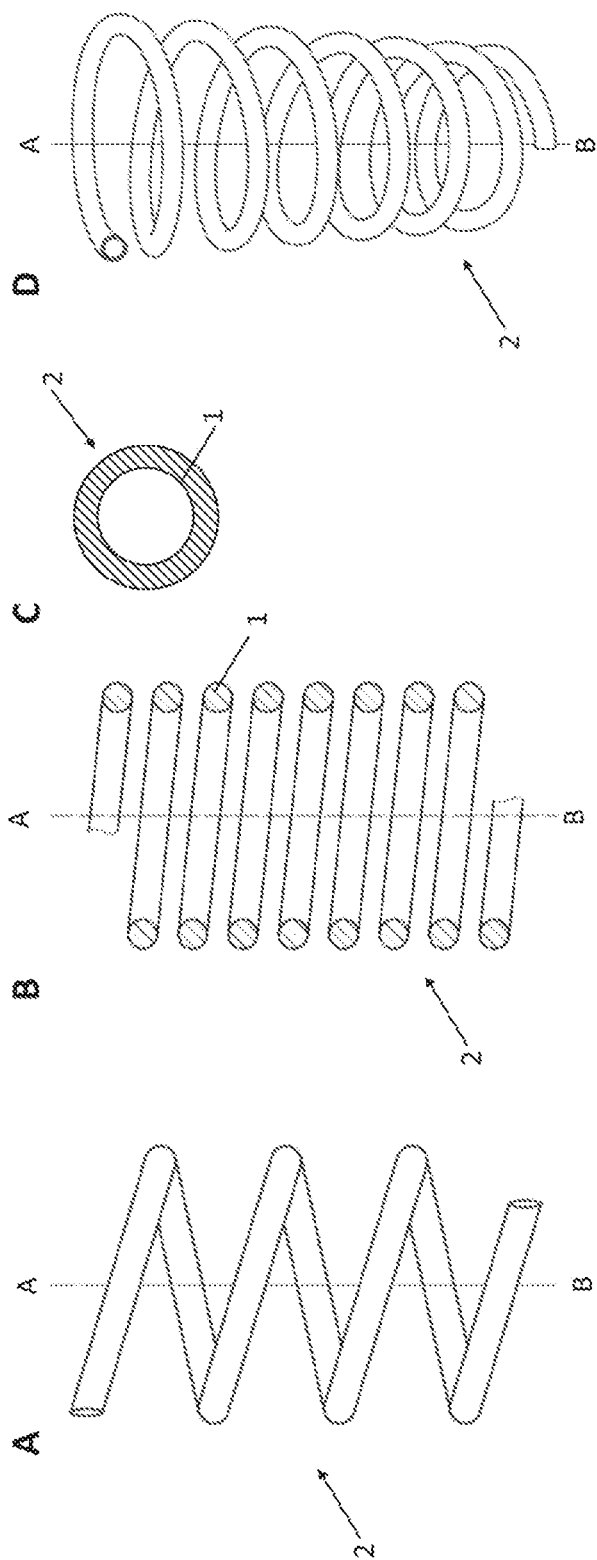
FIG. 3 illustrates a pipe 2 according to an embodiment of the invention. A illustrates a pipe 2 turning around a helical axis (AB) and comprising an inner polymer surface 1. B is a sectional view of a pipe 2 according to an embodiment of the invention. C is a sectional view of a pipe 2 comprising a polymer inner surface 1. D is a projected view a pipe 2 according to an embodiment of the invention.

In one embodiment, illustrated in FIGS. 3A-C, the polymer surface 1 is the inner surface of a pipe 2, a tube, a conduit, a duct, a gutter, an open-pipe, or a channel. In this embodiment, the pipe 2, tube, conduit, duct, gutter, open-pipe, or channel develop along a vertical axis.

According to one embodiment, the pipe 2 has a three-dimensional shape configured such that as a sample move forwards in the pipe 2, the gravitational potential energy of said sample decreases.

In one embodiment, the section of the pipe 2 has a circular or ovoidal shape.

In one embodiment, a portion of the pipe 2 has at least one dimension ranging from 1 mm to 1 cm. Said dimension may refer to the width, the section, the diameter or any other dimension of the pipe 2.

In one embodiment, a portion of the pipe 2 has at least one dimension of at least 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, 6.1 mm, 6.2 mm, 6.3 mm, 6.4 mm, 6.5 mm, 6.6 mm, 6.7 mm, 6.8 mm, 6.9 mm, 7 mm, 7.1 mm, 7.2 mm, 7.3 mm, 7.4 mm, 7.5 mm, 7.6 mm, 7.7 mm, 7.8 mm, 7.9 mm, 8 mm, 8.1 mm, 8.2 mm, 8.3 mm, 8.4 mm, 8.5 mm, 8.6 mm, 8.7 mm, 8.8 mm, 8.9 mm, 9 mm, 9.1 mm, 9.2 mm, 9.3 mm, 9.4 mm, 9.5 mm, 9.6 mm, 9.7 mm, 9.8 mm, 9.9 mm, or 1 cm.

In one embodiment, a portion of the pipe 2 has at least one dimension ranging from $1 \times 10^{-3}$ m to $1 \times 10^{-2}$ m.

In one embodiment, the section of the pipe 2 ranges from 1 $mm^2$ to 1 $cm^2$.

In one embodiment, the section of the pipe 2 is at least 1 $mm^2$, 1.1 $mm^2$, 1.2 $mm^2$, 1.3 $mm^2$, 1.4 $mm^2$, 1.5 $mm^2$, 1.6 $mm^2$, 1.7 $mm^2$, 1.8 $mm^2$, 1.9 $mm^2$, 2 $mm^2$, 2.1 $mm^2$, 2.2 $mm^2$, 2.3 $mm^2$, 2.4 $mm^2$, 2.5 $mm^2$, 2.6 $mm^2$, 2.7 $mm^2$, 2.8 mm², 2.9 mm², 3 mm², 3.1 mm², 3.2 mm², 3.3 mm², 3.4 mm², 3.5 mm², 3.6 mm², 3.7 mm², 3.8 mm², 3.9 mm², 4 mm², 4.1 mm², 4.2 mm², 4.3 mm², 4.4 mm², 4.5 mm², 4.6 mm², 4.7 mm², 4.8 mm², 4.9 mm², 5 mm², 5.1 mm², 5.2 mm², 5.3 mm², 5.4 mm², 5.5 mm², 5.6 mm², 5.7 mm², 5.8 mm², 5.9 mm², 6 mm², 6.1 mm², 6.2 mm², 6.3 mm², 6.4 mm², 6.5 mm², 6.6 mm², 6.7 mm², 6.8 mm², 6.9 mm², 7 mm², 7.1 mm², 7.2 mm², 7.3 mm², 7.4 mm², 7.5 mm², 7.6 mm², 7.7 mm², 7.8 mm², 7.9 mm², 8 mm², 8.1 mm², 8.2 mm², 8.3 mm², 8.4 mm², 8.5 mm², 8.6 mm², 8.7 mm², 8.8 mm², 8.9 mm², 9 mm², 9.1 mm², 9.2 mm², 9.3 mm², 9.4 mm², 9.5 mm², 9.6 mm², 9.7 mm², 9.8 mm², 9.9 mm², or 1 cm².

In one embodiment, the section of the pipe 2 ranges from $1\times10^{-6}$ m² to $1\times10^{-4}$ m².

In one embodiment, the length of the pipe 2 ranges from 10 cm to 100 cm.

In one embodiment, the length of the pipe 2 is at least 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, 25 cm, 26 cm, 27 cm, 28 cm, 29 cm, 30 cm, 31 cm, 32 cm, 33 cm, 34 cm, 35 cm, 36 cm, 37 cm, 38 cm, 39 cm, 40 cm, 41 cm, 42 cm, 43 cm, 44 cm, 45 cm, 46 cm, 47 cm, 48 cm, 49 cm, 50 cm, 51 cm, 52 cm, 53 cm, 54 cm, 55 cm, 56 cm, 57 cm, 58 cm, 59 cm, 60 cm, 61 cm, 62 cm, 63 cm, 64 cm, 65 cm, 66 cm, 67 cm, 68 cm, 69 cm, 70 cm, 71 cm, 72 cm, 73 cm, 74 cm, 75 cm, 76 cm, 77 cm, 78 cm, 79 cm, 80 cm, 81 cm, 82 cm, 83 cm, 84 cm, 85 cm, 86 cm, 87 cm, 88 cm, 89 cm, 90 cm, 91 cm, 92 cm, 93 cm, 94 cm, 95 cm, 96 cm, 97 cm, 98 cm, 99 cm, or 100 cm.

In one embodiment, the length of the pipe 2 ranges from $10\times10^{-2}$ m to 1 m.

In one embodiment, illustrated in FIGS. 3A-D, the pipe 2 is helical-shaped. In this embodiment, the pipe 2 is a vertical spiral pipe.

In one embodiment, the pipe 2 comprises at least one vertical helical-shaped portion.

In one embodiment, the pipe 2 comprises a plurality of vertical helical-shaped portions.

Figure 4:
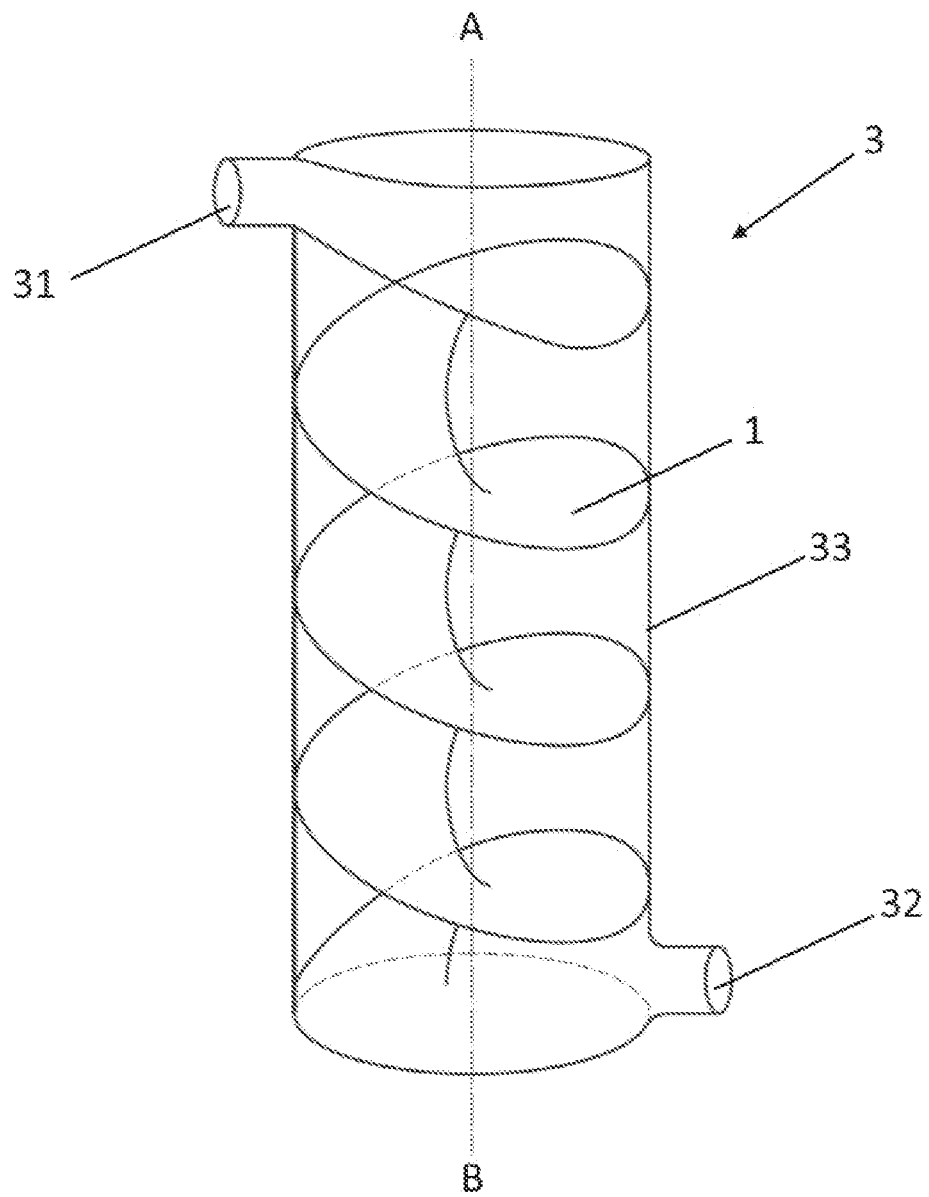
FIG. 4 illustrates an apparatus 3 comprising a polymer surface 1, comprising a helical-shaped portion, in a tube 33 comprising at least one inlet 31 and at least one outlet 32.

In one embodiment, illustrated in FIG. 4, the polymer surface 1 comprises at least one vertical helical-shaped portion.

In one embodiment, the polymer surface 1 comprises a plurality of vertical helical-shaped portions. This embodiment allows to increase the length of the polymer surface 1.

In one embodiment, the at least one vertical helical-shaped portion has a width ranging from 1 cm to 10 cm.

In one embodiment, the at least one vertical helical-shaped portion has a width of at least 1 cm, 1.1 cm, 1.2 cm, 1.3 cm, 1.4 cm, 1.5 cm, 1.6 cm, 1.7 cm, 1.8 cm, 1.9 cm, 2 cm, 2.1 cm, 2.2 cm, 2.3 cm, 2.4 cm, 2.5 cm, 2.6 cm, 2.7 cm, 2.8 cm, 2.9 cm, 3 cm, 3.1 cm, 3.2 cm, 3.3 cm, 3.4 cm, 3.5 cm, 3.6 cm, 3.7 cm, 3.8 cm, 3.9 cm, 4 cm, 4.1 cm, 4.2 cm, 4.3 cm, 4.4 cm, 4.5 cm, 4.6 cm, 4.7 cm, 4.8 cm, 4.9 cm, 5 cm, 5.1 cm, 5.2 cm, 5.3 cm, 5.4 cm, 5.5 cm, 5.6 cm, 5.7 cm, 5.8 cm, 5.9 cm, 6 cm, 6.1 cm, 6.2 cm, 6.3 cm, 6.4 cm, 6.5 cm, 6.6 cm, 6.7 cm, 6.8 cm, 6.9 cm, 7 cm, 7.1 cm, 7.2 cm, 7.3 cm, 7.4 cm, 7.5 cm, 7.6 cm, 7.7 cm, 7.8 cm, 7.9 cm, 8 cm, 8.1 cm, 8.2 cm, 8.3 cm, 8.4 cm, 8.5 cm, 8.6 cm, 8.7 cm, 8.8 cm, 8.9 cm, 9 cm, 9.1 cm, 9.2 cm, 9.3 cm, 9.4 cm, 9.5 cm, 9.6 cm, 9.7 cm, 9.8 cm, 9.9 cm, or 10 cm.

In one embodiment, the at least one vertical helical-shaped portion has a width ranging from $1\times10^{-2}$ m to $10\times10^{-2}$ m.

In one embodiment, the at least one vertical helical-shaped portion has a helical radius ranging from 0.5 cm to 5 cm.

In one embodiment, the at least one vertical helical-shaped portion has a helical radius of at least 0.5 cm, 0.6 cm, 0.7 cm, 0.8 cm, 0.9 cm, 1 cm, 1.1 cm, 1.2 cm, 1.3 cm, 1.4 cm, 1.5 cm, 1.6 cm, 1.7 cm, 1.8 cm, 1.9 cm, 2 cm, 2.1 cm, 2.2 cm, 2.3 cm, 2.4 cm, 2.5 cm, 2.6 cm, 2.7 cm, 2.8 cm, 2.9 cm, 3 cm, 3.1 cm, 3.2 cm, 3.3 cm, 3.4 cm, 3.5 cm, 3.6 cm, 3.7 cm, 3.8 cm, 3.9 cm, 4 cm, 4.1 cm, 4.2 cm, 4.3 cm, 4.4 cm, 4.5 cm, 4.6 cm, 4.7 cm, 4.8 cm, 4.9 cm, or 5 cm.

In one embodiment, the at least one vertical helical-shaped portion has a helical radius ranging from $0.5\times10^{-2}$ m to $5\times10^{-2}$ m.

In one embodiment, the vertical helical-shaped portions of the plurality of vertical helical-shaped portions have the same length, and/or section dimensions.

In one embodiment, the vertical helical-shaped portions of the plurality of vertical helical-shaped portions have the same helical radius.

In one embodiment, the vertical helical-shaped portions of the plurality of vertical helical-shaped portions turn around the same axis at the same and constant distance. In this embodiment, said axis is a vertical axis.

In one embodiment, the vertical helical-shaped portions of the plurality of vertical helical-shaped portions have distinct lengths, and/or section dimensions.

In one embodiment, the vertical helical-shaped portions of the plurality of vertical helical-shaped portions have distinct helical radii.

In one embodiment, the vertical helical-shaped portions of the plurality of vertical helical-shaped portions turn around the same axis at a distinct distance, said distance being constant or continuously varying for each vertical helical-shaped portion. In this embodiment, said axis is a vertical axis.

In one embodiment, the vertical helical-shaped portions of the plurality of vertical helical-shaped portions are attached, glued, screwed, clipped, or attached to each other by any means known by the person skilled in the art.

In one embodiment, the polymer surface 1 comprises at least one threaded shaped portion.

In one embodiment, the polymer surface 1 comprises at least one straight grooved shaped portion.

In one embodiment, the collector is configured to collect saline solution comprising purified mesenchymal stem cells.

In one embodiment, the collector is disposable.

In one embodiment, the collector is reusable. In this embodiment, said collector has to be cleaned following use.

In one embodiment, the collector is sterile.

In one embodiment, the collector is a container, a bottle, a tube, or a pouch.

In one embodiment, the solution resulting the first step, i.e. flowing a sample of adipose tissue on a polymer surface 1, is collected and/or eliminated.

In one embodiment, the solution resulting the first step, i.e. flowing a sample of adipose tissue on a polymer surface 1, is collected in a container, a bottle, a tube, or a pouch.

In one embodiment, the solution resulting the first step, i.e. flowing a sample of adipose tissue on a polymer surface 1, is eliminated after flowing.

In a second aspect, this invention relates to an apparatus 3 for purifying adipose-derived mesenchymal stem cells, comprising a polymer surface 1, preferably a polystyrene surface, wherein the polymer surface 1 comprises a geometrical design inducting a minimal flow rate when a control solution is introduced into said polymer surface 1.

In one embodiment, the apparatus of the invention is used to purify mesenchymal stem cells such as for example blood umbilical cord stem cells, molar stem cells, amniotic fluid stem cells, follicular stem cells, or human embryonic stem cells (hESC) obtained without the destruction of an embryo using a method such as for example the one described in Chung et al., Cell Stem Cell, Vol. 2 (2), pages 113-117, 2008.

In one embodiment, the apparatus 3 further comprises a lumen extending between at least one inlet 31 and at least one outlet 32, wherein the lumen comprises at least one portion of a polymer surface 1.

In one embodiment, the polymer surface 1 extends between at least one inlet 31 and at least one outlet 32, comprises a portion having at least one dimension ranging from 1 mm to 1 cm, and is the surface of a three-dimensional system configured such that as a sample moves forward on said polymer surface 1, the gravitational potential energy of said sample decreases on at least a portion of said polymer surface 1.

In one embodiment, a control solution may be for example a saline solution.

In one embodiment, examples of geometrical design include but are not limited to: helix, groove, or thread.

In one embodiment, the apparatus 3 is sterile.

In one embodiment, the apparatus 3 comprises a saline solution.

In one embodiment, the at least one inlet 31 and the at least one outlet 32 have a circular or ovoidal shape.

In one embodiment, the at least one inlet 31 and the at least one outlet 32 have the same shape.

In one embodiment, the at least one inlet 31 and the at least one outlet 32 have two distinct shapes.

In one embodiment, the at least one inlet 31 and/or the at least one outlet 32 have a portion with at least one dimension ranging from 1 mm to 1 cm.

In one embodiment, the at least one inlet 31 and/or the at least one outlet 32 have a portion with at least one dimension of at least 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, 6.1 mm, 6.2 mm, 6.3 mm, 6.4 mm, 6.5 mm, 6.6 mm, 6.7 mm, 6.8 mm, 6.9 mm, 7 mm, 7.1 mm, 7.2 mm, 7.3 mm, 7.4 mm, 7.5 mm, 7.6 mm, 7.7 mm, 7.8 mm, 7.9 mm, 8 mm, 8.1 mm, 8.2 mm, 8.3 mm, 8.4 mm, 8.5 mm, 8.6 mm, 8.7 mm, 8.8 mm, 8.9 mm, 9 mm, 9.1 mm, 9.2 mm, 9.3 mm, 9.4 mm, 9.5 mm, 9.6 mm, 9.7 mm, 9.8 mm, 9.9 mm, or 1 cm.

In one embodiment, the at least one inlet 31 and/or the at least one outlet 32 have a portion with at least one dimension ranging from $1\times10^{-3}$ m to $1\times10^{-2}$ m.

In one embodiment, the section of the at least one inlet 31 and/or the at least one outlet 32 ranges from 1 mm$^2$ to 1 cm$^2$.

In one embodiment, the section of the at least one inlet 31 and/or the at least one outlet 32 is at least 1 mm$^2$, 1.1 mm$^2$, 1.2 mm$^2$, 1.3 mm$^2$, 1.4 mm$^2$, 1.5 mm$^2$, 1.6 mm$^2$, 1.7 mm$^2$, 1.8 mm$^2$, 1.9 mm$^2$, 2 mm$^2$, 2.1 mm$^2$, 2.2 mm$^2$, 2.3 mm$^2$, 2.4 mm$^2$, 2.5 mm$^2$, 2.6 mm$^2$, 2.7 mm$^2$, 2.8 mm$^2$, 2.9 mm$^2$, 3 mm$^2$, 3.1 mm$^2$, 3.2 mm$^2$, 3.3 mm$^2$, 3.4 mm$^2$, 3.5 mm$^2$, 3.6 mm$^2$, 3.7 mm$^2$, 3.8 mm$^2$, 3.9 mm$^2$, 4 mm$^2$, 4.1 mm$^2$, 4.2 mm$^2$, 4.3 mm$^2$, 4.4 mm$^2$, 4.5 mm$^2$, 4.6 mm$^2$, 4.7 mm$^2$, 4.8 mm$^2$, 4.9 mm$^2$, 5 mm$^2$, 5.1 mm$^2$, 5.2 mm$^2$, 5.3 mm$^2$, 5.4 mm$^2$, 5.5 mm$^2$, 5.6 mm$^2$, 5.7 mm$^2$, 5.8 mm$^2$, 5.9 mm$^2$, 6 mm$^2$, 6.1 mm$^2$, 6.2 mm$^2$, 6.3 mm$^2$, 6.4 mm$^2$, 6.5 mm$^2$, 6.6 mm$^2$, 6.7 mm$^2$, 6.8 mm$^2$, 6.9 mm$^2$, 7 mm$^2$, 7.1 mm$^2$, 7.2 mm$^2$, 7.3 mm$^2$, 7.4 mm$^2$, 7.5 mm$^2$, 7.6 mm$^2$, 7.7 mm$^2$, 7.8 mm$^2$, 7.9 mm$^2$, 8 mm$^2$, 8.1 mm$^2$, 8.2 mm$^2$, 8.3 mm$^2$, 8.4 mm$^2$, 8.5 mm$^2$, 8.6 mm$^2$, 8.7 mm$^2$, 8.8 mm$^2$, 8.9 mm$^2$, 9 mm$^2$, 9.1 mm$^2$, 9.2 mm$^2$, 9.3 mm$^2$, 9.4 mm$^2$, 9.5 mm$^2$, 9.6 mm$^2$, 9.7 mm$^2$, 9.8 mm$^2$, 9.9 mm$^2$, or 1 cm$^2$.

In one embodiment, the section of the at least one inlet 31 and/or the at least one outlet 32 ranges from $1\times10^{-6}$ m$^2$ to $1\times10^{-4}$ m$^2$.

In one embodiment, the at least one inlet 31 and the at least one outlet 32 have the same section.

In one embodiment, the at least one inlet 31 and the at least one outlet 32 have two distinct sections.

In one embodiment, the polymer surface 1 is as described hereabove.

In one embodiment, the polymer surface 1 is the inner surface of a pipe 2, a tube, a conduit, a duct, a gutter, an open-pipe, or a channel. In this embodiment, the apparatus 3 is a pipe 2.

In one embodiment, the pipe 2 is as described hereabove.

In one embodiment, as illustrated in FIG. 4, the apparatus 3 comprises a polymer surface 1 comprising a vertical helical-shaped portion in a tube 33 comprising at least one inlet 31 and at least one outlet 32.

Tube (33, 34, 35) hereafter refers to a tube, a container, or a centrifugation tube.

In one embodiment, the at least one inlet 31 and the at least one outlet 32 are located at two distinct levels on said tube 33.

In one embodiment, the longitudinal axis (AB) of the tube 33 is the helical axis of the at least one vertical helical-shaped portion of the polymer surface 1. In this embodiment, said axis (AB) is a vertical axis.

Figure 5:
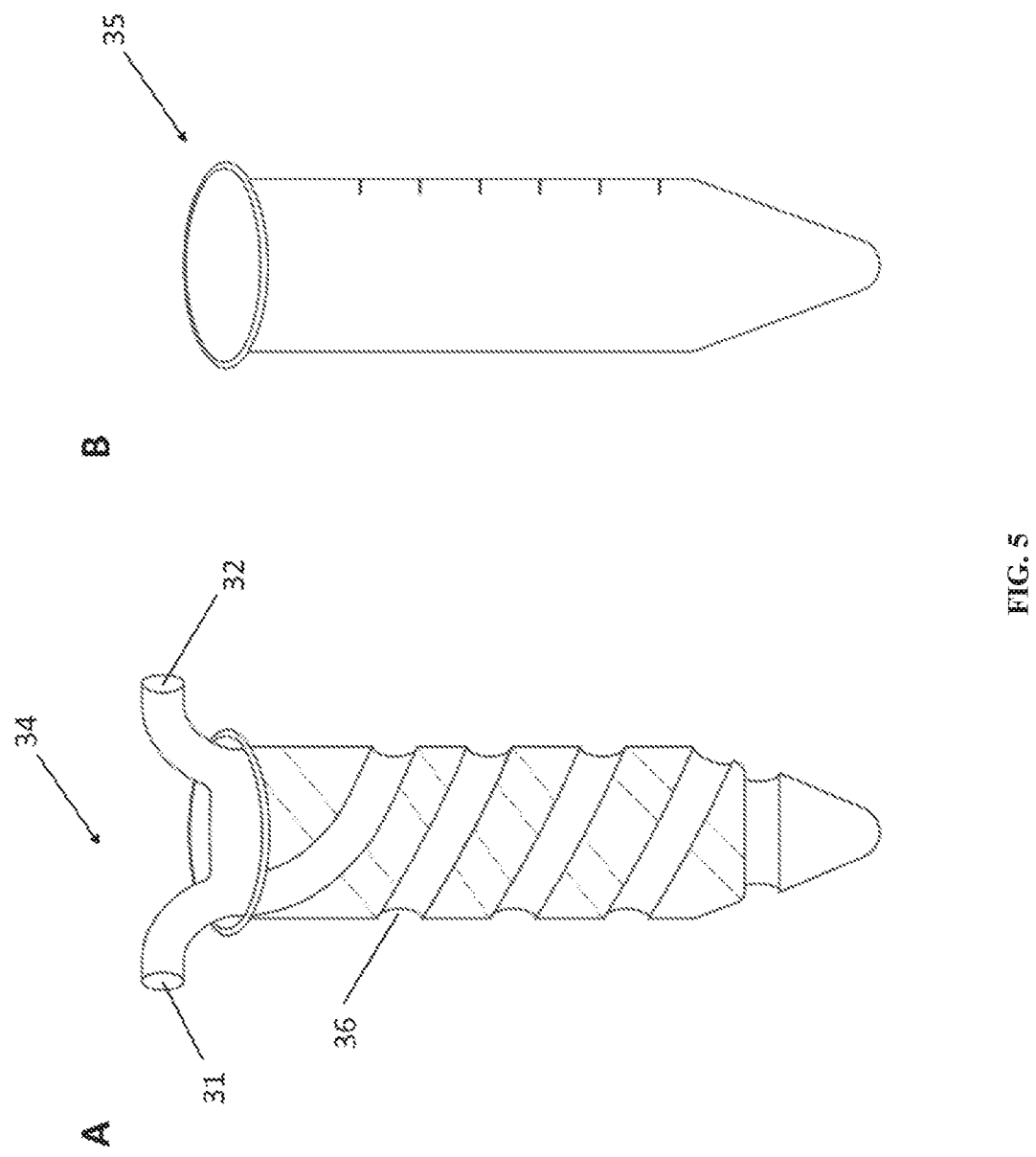
FIG. 5 illustrates an apparatus 3 comprising an outer tube 35 and an inner tube 34; said inner tube 34 comprising a polymer threaded groove 36 extending between an inlet 31 and an outlet 32. A illustrates an inner tube 34 comprising a polymer threaded groove 36 extending between an inlet 31 and an outlet 32. B illustrates an outer tube 35 of the apparatus 3.
Figure 6:
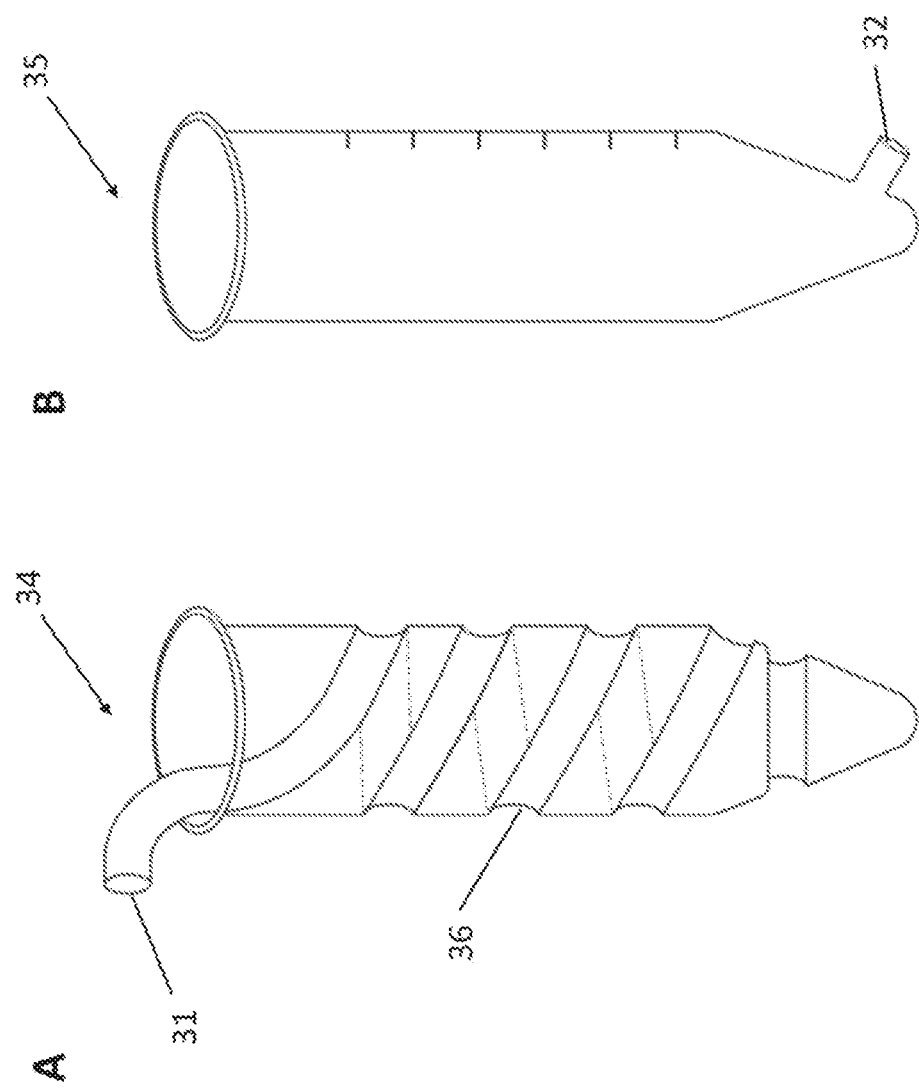
FIG. 6 illustrates an apparatus 3 comprising an outer tube 35 and an inner tube 34; said inner tube 34 comprising a polymer threaded groove 36 extending between an inlet 31 and an outlet 32. A illustrates an inner tube 34 comprising a polymer threaded groove 36 extending between an inlet 31 and an outlet 32. B illustrates an outer tube 35 comprising an outlet 32.
Figure 7:
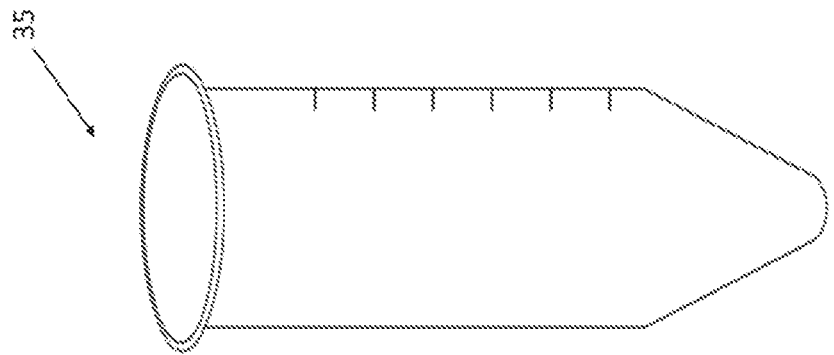
FIG. 7 illustrates an apparatus 3 comprising an outer tube 35 and an inner tube 34; said inner tube 34 comprising a polymer straight groove 36 extending between an inlet 31 and an outlet 32. A illustrates an inner tube 34 comprising a polymer straight groove 36 extending between an inlet 31 and an outlet 32. B illustrates an outer tube 35 of the apparatus 3.
Figure 7:
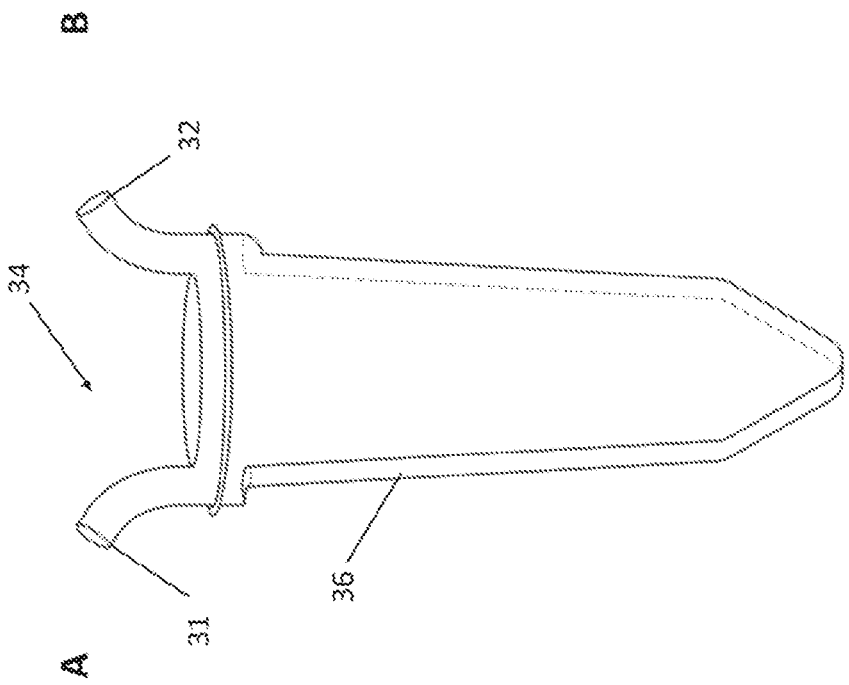

In one embodiment, illustrated in FIGS. 5-7, the apparatus 3 comprises an outer tube 35 and an inner tube 34; said inner tube 34 comprising a polymer groove 36 extending between at least one inlet 31 and at least one outlet 32. In this embodiment, the polymer surface 1 is a polymer groove 36.

In one embodiment, the outer tube 35 is configured to receive the inner tube 34 (FIGS. 5B, 6B and 7B). In this embodiment, when the inner tube 34 is inserted in the outer tube 35, the polymer groove 36 forms a channel.

In one embodiment, the inner tube 34 is inserted in the outer tube 35, and the tubes (34, 35) are glued, sealed or welded together.

In one embodiment, illustrated in FIGS. 5 and 6, the polymer surface 1 has a threaded shape. In this embodiment, the polymer groove 36 is threaded along the inner tube 34. Thus, the channel is a threaded channel extending between the at least one inlet 31 and the at least one outlet 32. This embodiment allows a long channel and more cells to polymer contact, the deceleration of the stem cells is more effective.

In one embodiment, illustrated in FIG. 7, the polymer surface 1 has a straight grooved shape. In this embodiment, the polymer groove 36 is straight along the inner tube 34. Thus, the channel is a straight channel extending between the at least one inlet 31 and the at least one outlet 32.

In one embodiment, the channel has a portion having at least one dimension ranging from 1 mm to 1 cm.

In one embodiment, the channel has a portion having at least one dimension of at least 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, 6.1 mm, 6.2 mm, 6.3 mm, 6.4 mm, 6.5 mm, 6.6 mm, 6.7 mm, 6.8 mm, 6.9 mm, 7 mm, 7.1 mm, 7.2 mm, 7.3 mm, 7.4 mm, 7.5 mm, 7.6 mm, 7.7 mm, 7.8 mm, 7.9 mm, 8 mm, 8.1 mm, 8.2 mm, 8.3 mm, 8.4 mm, 8.5 mm, 8.6 mm, 8.7 mm, 8.8 mm, 8.9 mm, 9 mm, 9.1 mm, 9.2 mm, 9.3 mm, 9.4 mm, 9.5 mm, 9.6 mm, 9.7 mm, 9.8 mm, 9.9 mm, or 1 cm.

In one embodiment, the channel has a portion having at least one dimension ranging from $1 \times 10^{-3}$ m to $1 \times 10^{-2}$ m.

In one embodiment, the section of the channel ranges from 1 mm$^2$ to 1 cm$^2$.

In one embodiment, the section of the channel is at least 1 mm$^2$, 1.1 mm$^2$, 1.2 mm$^2$, 1.3 mm$^2$, 1.4 mm$^2$, 1.5 mm$^2$, 1.6 mm$^2$, 1.7 mm$^2$, 1.8 mm$^2$, 1.9 mm$^2$, 2 mm$^2$, 2.1 mm$^2$, 2.2 mm$^2$, 2.3 mm$^2$, 2.4 mm$^2$, 2.5 mm$^2$, 2.6 mm$^2$, 2.7 mm$^2$, 2.8 mm$^2$, 2.9 mm$^2$, 3 mm$^2$, 3.1 mm$^2$, 3.2 mm$^2$, 3.3 mm$^2$, 3.4 mm$^2$, 3.5 mm$^2$, 3.6 mm$^2$, 3.7 mm$^2$, 3.8 mm$^2$, 3.9 mm$^2$, 4 mm$^2$, 4.1 mm$^2$, 4.2 mm$^2$, 4.3 mm$^2$, 4.4 mm$^2$, 4.5 mm$^2$, 4.6 mm$^2$, 4.7 mm$^2$, 4.8 mm$^2$, 4.9 mm$^2$, 5 mm$^2$, 5.1 mm$^2$, 5.2 mm$^2$, 5.3 mm$^2$, 5.4 mm$^2$, 5.5 mm$^2$, 5.6 mm$^2$, 5.7 mm$^2$, 5.8 mm$^2$, 5.9 mm$^2$, 6 mm$^2$, 6.1 mm$^2$, 6.2 mm$^2$, 6.3 mm$^2$, 6.4 mm$^2$, 6.5 mm$^2$, 6.6 mm$^2$, 6.7 mm$^2$, 6.8 mm$^2$, 6.9 mm$^2$, 7 mm$^2$, 7.1 mm$^2$, 7.2 mm$^2$, 7.3 mm$^2$, 7.4 mm$^2$, 7.5 mm$^2$, 7.6 mm$^2$, 7.7 mm$^2$, 7.8 mm$^2$, 7.9 mm$^2$, 8 mm$^2$, 8.1 mm$^2$, 8.2 mm$^2$, 8.3 mm$^2$, 8.4 mm$^2$, 8.5 mm$^2$, 8.6 mm$^2$, 8.7 mm$^2$, 8.8 mm$^2$, 8.9 mm$^2$, 9 mm$^2$, 9.1 mm$^2$, 9.2 mm$^2$, 9.3 mm$^2$, 9.4 mm$^2$, 9.5 mm$^2$, 9.6 mm$^2$, 9.7 mm$^2$, 9.8 mm$^2$, 9.9 mm$^2$, or 1 cm$^2$.

In one embodiment, the section of the channel ranges from $1 \times 10^{-6}$ m$^2$ to $1 \times 10^{-4}$ m$^2$.

In one embodiment, the channel is not a microfluidic channel.

In one embodiment, the channel has length ranging from 10 cm to 100 cm.

In one embodiment, the channel has length of at least 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, 25 cm, 26 cm, 27 cm, 28 cm, 29 cm, 30 cm, 31 cm, 32 cm, 33 cm, 34 cm, 35 cm, 36 cm, 37 cm, 38 cm, 39 cm, 40 cm, 41 cm, 42 cm, 43 cm, 44 cm, 45 cm, 46 cm, 47 cm, 48 cm, 49 cm, 50 cm, 51 cm, 52 cm, 53 cm, 54 cm, 55 cm, 56 cm, 57 cm, 58 cm, 59 cm, 60 cm, 61 cm, 62 cm, 63 cm, 64 cm, 65 cm, 66 cm, 67 cm, 68 cm, 69 cm, 70 cm, 71 cm, 72 cm, 73 cm, 74 cm, 75 cm, 76 cm, 77 cm, 78 cm, 79 cm, 80 cm, 81 cm, 82 cm, 83 cm, 84 cm, 85 cm, 86 cm, 87 cm, 88 cm, 89 cm, 90 cm, 91 cm, 92 cm, 93 cm, 94 cm, 95 cm, 96 cm, 97 cm, 98 cm, 99 cm, or 100 cm.

In one embodiment, the channel has length ranging from $10 \times 10^{-2}$ m to 1 m.

In one embodiment, the at least one inlet 31 and the at least one outlet 32 are located at the same level on the apparatus 3 (FIGS. 5A and 7A).

In one embodiment, illustrated in FIGS. 6A-B, the at least one inlet 31 and the at least one outlet 32 are located at a distinct level on the apparatus 3, said at least one outlet 32 being located at a level inferior to the one of the at least one inlet 31. In this embodiment, when the sample moves forward in said channel, the gravitational potential energy of said sample decreases.

In one embodiment, illustrated in FIGS. 5A and 7A, the at least one inlet 31 and the at least one outlet 32 are located on the inner tube 34.

In one embodiment, the inner tube 34 has a conical or rounded end.

In one embodiment, the outer tube 35 has a conical or rounded end.

In one embodiment, the outer tube 35 does not comprise an inlet 31 or an outlet 32 (FIGS. 5B and 7B).

In one embodiment, illustrated in FIG. 6B, the inner tube 34 comprises at least one inlet 31 for the sample and the outer tube 35 comprises at least one outlet 32.

According to one embodiment, the apparatus 3 comprises two inlets 31. According to another embodiment, the apparatus 3 comprises two outlets 32.

In one embodiment, the apparatus 3 does not comprise any pumping means. In this embodiment, the gravity only is sufficient to push the sample or saline solution along the polymer surface 1.

In one embodiment, the apparatus 3 further comprises at least one pumping means configured to supply said apparatus 3 with the at least one sample and/or the at least one saline solution.

In one embodiment, the apparatus 3 further comprises two pumping means: a first pumping means configured to supply said apparatus 3 with the at least one sample and a second pumping means configured to supply said apparatus 3 with the at least one saline solution.

In one embodiment, the at least one pumping means is a mechanical pumping means.

In one embodiment, the at least one pumping means is a pump, a syringe pump, a peristaltic pump, or a piezoelectric type of pump.

In one embodiment, the apparatus 3 is not a microfluidic structure.

In one embodiment, the apparatus 3 does not comprise a microfluidic structure.

In a third aspect, the invention relates to the use of the apparatus 3 as described hereabove for purifying adipose-derived mesenchymal stem cells. In particular, the apparatus 3 may be used for purifying mesenchymal stem cells from isolated mesenchymal stem cells in order to use the purified stem cells in clinical application in situ.

In a fourth aspect, the invention relates to a system for purification of adipose-derived mesenchymal stem cells.

The system comprises:
an apparatus 3 as described hereabove;
at least one supplier fluidly connected to the at least one inlet 31 of the apparatus 3 and configured to be fluidly connected to at least one reservoir comprising at least one sample comprising mesenchymal stem cells and to at least one reservoir comprising at least one saline solution;
at least one collector fluidly connected to the at least one outlet 32 of the apparatus 3;
at least one flow controller configured to control the flow rate of a fluid passing through the supplier either at a first flow rate or at a second flow rate; and The first flow rate is slower than the second flow rate. The first flow rate is ranging from 10 to 150 ml/min. The second flow rate is ranging from 100 to 500 ml/min.

In one embodiment, the first flow rate and the second flow rate are as described hereabove.

In one embodiment, the system implements the method of purifying adipose-derived mesenchymal stem cells as described hereabove.

In one embodiment, the system of the invention is used to purify mesenchymal stem cells such as for example blood umbilical cord stem cells, molar stem cells, amniotic fluid stem cells, follicular stem cells, or human embryonic stem cells (hESC) obtained without the destruction of an embryo using a method such as for example the one described in Chung et al., Cell Stem Cell, Vol. 2 (2), pages 113-117, 2008.

In one embodiment, the system optionally comprises a flowcytometer.

In one embodiment, the system is portable. In this embodiment, said system may be easily transported.

In one embodiment, the system is compliant with requirements of a sterile environment.

In one embodiment, the supplier comprises at least one tubing.

In one embodiment, the at least one tubing has a length ranging from 10 cm to 100 cm.

In one embodiment, the at least one tubing has a length of at least 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, 25 cm, 26 cm, 27 cm, 28 cm, 29 cm, 30 cm, 31 cm, 32 cm, 33 cm, 34 cm, 35 cm, 36 cm, 37 cm, 38 cm, 39 cm, 40 cm, 41 cm, 42 cm, 43 cm, 44 cm, 45 cm, 46 cm, 47 cm, 48 cm, 49 cm, 50 cm, 51 cm, 52 cm, 53 cm, 54 cm, 55 cm, 56 cm, 57 cm, 58 cm, 59 cm, 60 cm, 61 cm, 62 cm, 63 cm, 64 cm, 65 cm, 66 cm, 67 cm, 68 cm, 69 cm, 70 cm, 71 cm, 72 cm, 73 cm, 74 cm, 75 cm, 76 cm, 77 cm, 78 cm, 79 cm, 80 cm, 81 cm, 82 cm, 83 cm, 84 cm, 85 cm, 86 cm, 87 cm, 88 cm, 89 cm, 90 cm, 91 cm, 92 cm, 93 cm, 94 cm, 95 cm, 96 cm, 97 cm, 98 cm, 99 cm, or 100 cm.

In one embodiment, the at least one tubing has a length ranging from $10 \times 10^{-2}$ m to 1 m.

In one embodiment, the at least one tubing has a diameter ranging from 0.1 cm to 3 cm.

In one embodiment, the at least one tubing has a diameter of at least 0.1 cm, 0.2 cm, 0.3 cm, 0.4 cm, 0.5 cm, 0.6 cm, 0.7 cm, 0.8 cm, 0.9 cm, 1 cm, 1.1 cm, 1.2 cm, 1.3 cm, 1.4 cm, 1.5 cm, 1.6 cm, 1.7 cm, 1.8 cm, 1.9 cm, 2 cm, 2.1 cm, 2.2 cm, 2.3 cm, 2.4 cm, 2.5 cm, 2.6 cm, 2.7 cm, 2.8 cm, 2.9 cm, or 3 cm.

In one embodiment, the at least one tubing has a diameter ranging from $0.1 \times 10^{-2}$ m to $3 \times 10^{-2}$ m.

In one embodiment, the supplier is fluidly connected to the at least one inlet 31 of the apparatus 3 by clipping, gluing, or any attachment means.

In one embodiment, the supplier is fluidly connected to the at least one reservoir comprising at least one sample by clipping, gluing, or any attachment means.

In one embodiment, the supplier is fluidly connected to the at least one reservoir comprising at least one saline solution by clipping, gluing, or any attachment means.

In one embodiment, the at least one reservoir comprising at least one sample is sterile.

In one embodiment, the at least one reservoir comprising at least one sample is a container, a bottle, a tube, or a pouch.

In one embodiment, the at least one reservoir comprising at least one sample is clipped to the system.

In one embodiment, the at least one reservoir comprising at least one saline solution is sterile.

In one embodiment, the at least one reservoir comprising at least one saline solution is a container, a bottle, a tube, or a pouch.

In one embodiment, the at least one reservoir comprising at least one saline solution is clipped to the system.

In one embodiment, the at least one reservoir comprising at least one sample and/or the at least one reservoir comprising at least one saline solution is disposable.

In one embodiment, the at least one reservoir comprising at least one sample and/or the at least one reservoir comprising at least one saline solution is reusable. In this embodiment, said reservoir has to be cleaned following use.

In one embodiment, the at least one reservoir comprising at least one sample and/or the at least one reservoir comprising at least one saline solution is sterile.

In one embodiment, the at least one collector is fluidly connected to the at least one outlet 32 of the apparatus 3 by clipping, gluing, or any attachment means.

In one embodiment, the at least one collector is configured to collect the first flow passing in the apparatus 3.

In one embodiment, the at least one collector is configured to collect the second flow passing in the apparatus 3, i.e. the suspension of purified mesenchymal stem cells.

In one embodiment, the apparatus 3 comprises two collectors: a first collector configured to collect the first flow passing in the apparatus 3, and a second collector configured to collect the second flow passing in the apparatus 3, i.e. the suspension of purified mesenchymal stem cells.

In one embodiment, the at least one collector is disposable.

In one embodiment, the at least one collector is reusable. In this embodiment, said at least one collector has to be cleaned following use.

In one embodiment, the at least one collector is sterile.

In one embodiment, the at least one collector is a container, a bottle, a tube, or a pouch.

In one embodiment, the at least one flow controller is a flow meter.

In one embodiment, the at least one flow controller comprises at least one switch configured to switch on and off the first flow and/or the second flow.

In one embodiment, the at least one flow controller comprises at least one output switch located at the at least one output of the apparatus 3 configured to allow a fluid to pass from said apparatus 3 to the at least one collector.

In one embodiment, the at least one flow controller comprises at least one sensor configured to measure the first flow and/or the second flow.

In one embodiment, the at least one flow controller comprises at least one bubble trap.

In one embodiment, the at least one flow controller comprises at least one optical reader to display the measure of the flow.

In one embodiment, the system further comprises at least one pumping means configured to supply the apparatus 3 with the at least one sample and/or the at least one saline solution.

In one embodiment, the apparatus 3 comprises two inlets 31 and the supplier comprises two tubing; a first tubing configured to fluidly connect the first inlet 31 to at least one sample comprising mesenchymal stem cells and the second tubing configured to fluidly connect the second inlet 31 to at least one saline solution.

In one embodiment, the at least one flow controller is configured to flow a fluid passing through the first tubing at a first flow rate and to flow a fluid passing through the second tubing at a second flow rate, wherein the first flow rate is slower than the second flow rate.

In one embodiment, the system further comprises two pumping means: a first pumping means configured to supply the apparatus 3 with the at least one sample and a second pumping means configured to supply the apparatus 3 with the at least one saline solution.

In one embodiment, the at least one pumping means is a mechanical pumping means.

In one embodiment, the at least one pumping means is a pump, a syringe pump, a peristaltic pump, or a piezoelectric type of pump.

In one embodiment, the system further comprises a control unit, said control unit comprises a software configured to control the flow rates. In this embodiment, the software may control the first flow rate, the second flow rate, or the pressure delivered by the at least one pumping means. In this embodiment, the method implemented by the system may be semi-automated or automated. In this embodiment, the method implemented by the system may be a computer implemented method.

In one embodiment, the system further comprises an optical sensor configured to evaluate the quality of the suspension of purified mesenchymal stem cells.

In one embodiment, the system further comprises a flow-cytometer configured to measure the quantity and/or concentration of mesenchymal stem cells in the suspension of purified mesenchymal stem cells. In this embodiment, the quantity of purified mesenchymal stem cells may be measured for each sample. This will allow a personalized and more efficient use of the resulting suspension of purified mesenchymal stem cells. Indeed, this may lead the user to the decision to take an additional sample to have more cells available and reach a therapeutic threshold.

In one embodiment, the system further comprises a derivation tube located at or near the outlet 32 configured to fluidly connect the flowcytometer to the apparatus 3. Said derivation tube may pass through a reading chamber where the quantity of mesenchymal stem cells in the suspension of purified mesenchymal stem cells can be measured. In this embodiment, a tag or a cell marker can be added to said suspension to tag mesenchymal stem cells, this step may be manual or automated.

In one embodiment, the at least one output switch of the at least one flow controller is controlled by the software according to the evaluation performed by the optical sensor. In this embodiment, the output switch will allow the fluid to pass from the apparatus 3 to at least one collector configured to collect the suspension of purified mesenchymal stem cells if the mesenchymal stem cells are purified and free of cellular debris.

Figure 8:
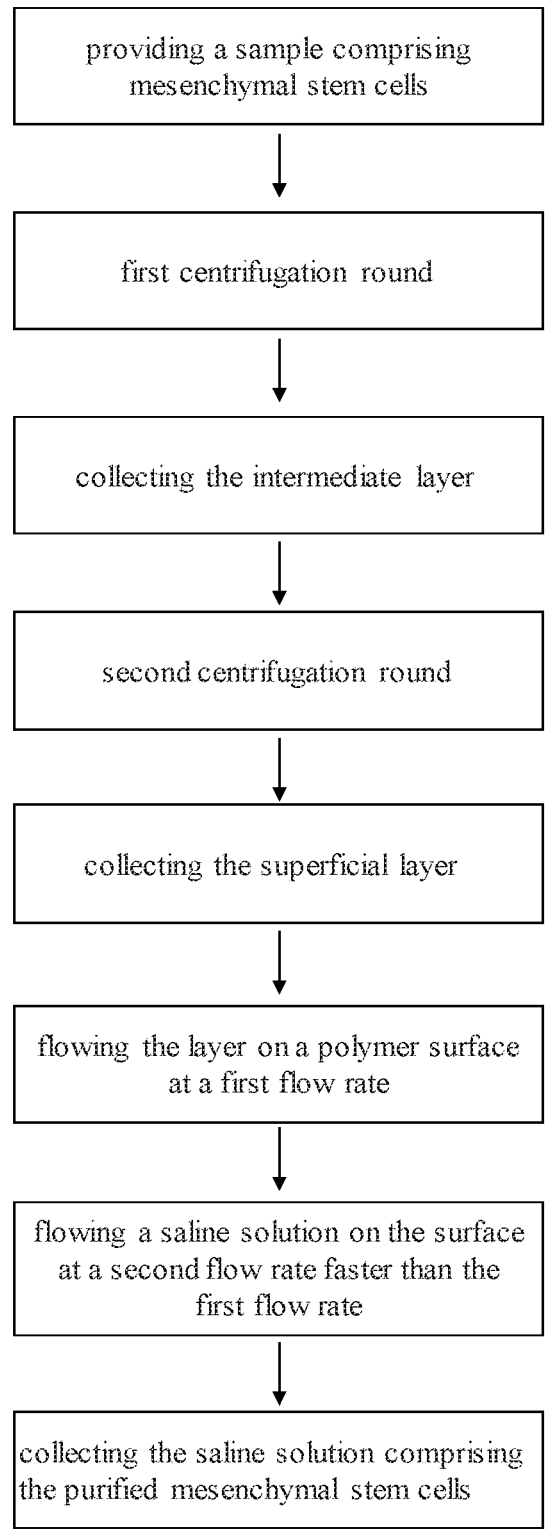
FIG. 8 is a histogram showing the method of isolating and purifying adipose-derived mesenchymal stem cells from adipose tissue according to the invention.

In a fifth aspect, illustrated in FIG. 8, the invention relates to a method of isolating and purifying adipose-derived mesenchymal stem cells from a sample of adipose tissue, comprising the steps of:
  subjecting the sample to at least one centrifugation round;
  collecting the centrifuged layer comprising mesenchymal stem cells;
  flowing said layer comprising mesenchymal stem cells on a polymer surface 1, preferably a polystyrene surface, at a first flow rate allowing separating said sample into a first remaining sample comprising mesenchymal stem cells on the polymer surface 1 and into a second resulting solution being evacuated from the polymer surface 1;
  flowing a saline solution on said polymer surface 1 at a second flow rate; and
  collecting the saline solution comprising purified mesenchymal stem cells in at least one collector.

The first flow rate is slower than the second flow rate. The first flow rate is ranging from 10 to 150 ml/min. The second flow rate is ranging from 100 to 500 ml/min.

The aim of the centrifugation step is to isolate mesenchymal stem cells prior purification using a polymer surface 1. Thus, the step of isolation of said mesenchymal stem cells is mechanical and do not use any chemicals or enzymes. This embodiment prevents a chemical modification or pollution of the stem cells.

The purified mesenchymal stem cells may be delivered immediately to different specialists for the treatment of a variety of conditions, for instance in orthopedics (joint diseases, bone grafts), ophthalmology (macular degeneration, glaucoma), uro-gynecology (urinary incontinence, erectile dysfunction), plastic surgery (face peels, hair regrowth, scars, lipofilling, lipostructure, breast augmentation), wound healing, salivary glands stimulation after radiotherapy, peripheral arterial disease. The purified mesenchymal stem cells may be reinjected in the subject that provided the sample of adipose tissue. They may be injected in joints, salivary glands, retina, skin, muscle, or mixed with bone graft. These cells may be used for any tissue regeneration procedure or method. They may also be topically applied on wounds, burn wounds, ulcers, after chemical or mechanical face peeling.

In one embodiment, the method of the invention is used to isolate and purify mesenchymal stem cells such as for example blood umbilical cord stem cells, molar stem cells, amniotic fluid stem cells, follicular stem cells, or human embryonic stem cells (hESC) obtained without the destruction of an embryo using a method such as for example the one described in Chung et al., Cell Stem Cell, Vol. 2 (2), pages 113-117, 2008.

In one embodiment, the method is chemical-free and enzyme-free. In this embodiment, the method is compliant with the requirements of Regulation (EC) no 1394/2007 of the European Parliament and of the Council of 13 Nov. 2007 on advanced therapy medicinal products. This embodiment prevents a chemical modification or pollution of the stem cells.

In one embodiment, the method is performed in less than 30 minutes. This method is very fast and allow the use the purified stem cells in clinical application in situ: the sample of adipose tissue can be provided and the resulting stem cells can be purified during the same clinical procedure.

In one embodiment, the method is performed in less than 30 minutes, 25 minutes, 20 minutes, 15 minutes, 10 minutes, or 5 minutes.

In one embodiment, the method is fully performed in less than 30 minutes. This method is very fast and allow the use the purified stem cells in clinical application in situ: the sample of adipose tissue can be provided and the resulting stem cells can be purified during the same clinical procedure.

In one embodiment, the method is fully performed in less than 30 minutes, 25 minutes, 20 minutes, 15 minutes, 10 minutes, or 5 minutes.

In one embodiment, the method of present invention is manual.

In one embodiment, the method of present invention is semi-automated.

In one embodiment, the method of present invention is automated.

In one embodiment, the first flow rate and the second flow rate are as described hereabove.

In one embodiment, the saline solution is as described hereabove.

In one embodiment, the sample of adipose tissue is a lipoaspirate.

In one embodiment, the method further comprises a step of providing a sample comprising adipose tissue. In this embodiment, the sample is provided prior subjecting said sample to at least one centrifugation round.

In one embodiment, the sample of adipose tissue is obtained by a minimally invasive procedure such as lipoaspiration, or minimally invasive surgery. In this embodiment, surgery may comprise incision and dissection. The abundance of adipose tissue and the minimally invasive procedure to provide it allows sampling of a large amount of adipose tissue to reach a mesenchymal stem cells therapeutic threshold.

In one embodiment, the sample of adipose tissue is obtained by any means known by the person skilled in the art.

In one embodiment, the sample has a volume ranging from 20 cm$^3$ to 200 cm$^3$.

In one embodiment, the sample has a volume of at least 20 cm$^3$, 30 cm$^3$, 40 cm$^3$, 50 cm$^3$, 60 cm$^3$, 70 cm$^3$, 80 cm$^3$, 90 cm$^3$, 100 cm$^3$, 110 cm$^3$, 120 cm$^3$, 130 cm$^3$, 140 cm$^3$, 150 cm$^3$, 160 cm$^3$, 170 cm$^3$, 180 cm$^3$, 190 cm$^3$, or 200 cm$^3$.

In one embodiment, the sample has a volume ranging from $20 \times 10^{-6}$ m$^3$ to $200 \times 10^{-6}$ m$^3$.

In one embodiment, the sample comprises unpurified mesenchymal stem cells. In this embodiment, the sample may comprise mesenchymal stem cells, cellular debris, extracellular matrix product, pre-adipocytes, leucocytes, endothelial cells, smooth muscle cells, pericytes, fibroblasts, erythrocytes, B and T cells, macrophages, monocytes, or mast cells.

In one embodiment, the steps of flowing the layer of mesenchymal stem cells on a polymer surface 1 and flowing a saline solution on said polymer surface 1 are as described hereabove.

In one embodiment, the polymer surface 1 is as described hereabove.

In one embodiment, the saline solution comprising the purified mesenchymal stem cells is collected as described hereabove.

According to one embodiment, the sample of adipose tissue is beforehand mixed with a saline solution at a temperature between 25° C. and 41° C.

According to one embodiment, the sample of adipose tissue is beforehand mixed with a saline solution at a temperature of at least 25° C., 26° C., 27° C., 28° C., 29° C., 30° C., 31° C., 32° C., 33° C., 34° C., 35° C., 36° C., 37° C., 38° C., 39° C., 40° C., or 41° C.

According to one embodiment, the sample of adipose tissue is beforehand mixed with a saline solution and water at a temperature between 25° C. and 41° C.

According to one embodiment, the sample of adipose tissue is beforehand mixed with a saline solution and water at a temperature of at least 25° C., 26° C., 27° C., 28° C., 29° C., 30° C., 31° C., 32° C., 33° C., 34° C., 35° C., 36° C., 37° C., 38° C., 39° C., 40° C., or 41° C.

According to one embodiment, saline solution and water are used in same quantity.

According to one embodiment, after mixing the sample of adipose tissue with a saline solution and/or water, said sample is heated and agitated.

In one embodiment, said sample is heated and agitated at a temperature ranging from 25° C. to 41° C. for at least 5 minutes.

In one embodiment, said sample is heated and agitated at a temperature of at least 25° C., 26° C., 27° C., 28° C., 29° C., 30° C., 31° C., 32° C., 33° C., 34° C., 35° C., 36° C., 37° C., 38° C., 39° C., 40° C., or 41° C. for at least 5 minutes.

In a preferred embodiment, said sample is heated and agitated at 39° C. for 10 minutes.

In one embodiment, said sample is heated and agitated in a vortex heating chamber.

In one embodiment, the step of subjecting the sample to at least one centrifugation round comprises the steps of:
subjecting the sample comprising adipose tissue to a first centrifugation round;
collecting the intermediate centrifuged layer;
subjecting said intermediate centrifuged layer to a second centrifugation round; and
collecting the superficial centrifuged layer comprising stem cells.

The two centrifugation rounds allow the separation of the stem cells from the other populations.

In one embodiment, the at least one centrifugation round is performed at a rate below 1500 rounds per minute.

In one embodiment, the at least one centrifugation round is performed at a rate below 1500 rounds per minute, 1400 rounds per minute, 1300 rounds per minute, 1200 rounds per minute, 1100 rounds per minute, 1000 rounds per minute, 900 rounds per minute, 800 rounds per minute, 700 rounds per minute, 600 rounds per minute, or 500 rounds per minute.

In one embodiment, the at least one centrifugation round is performed for a time ranging from 3 to 20 min.

In one embodiment, the at least one centrifugation round is performed for at least 3 min, 4 min, 5 min, 6 min, 7 min, 8 min, 9 min, 10 min, 11 min, 12 min, 13 min, 14 min, 15 min, 16 min, 17 min, 18 min, 19 min, or 20 min.

In one embodiment, the first and the second centrifugation rounds are preferably performed at a rate below 1500 rounds per minute. It is known that a strong centrifugation, over 1500 rounds per minute will precipitate the stem cells with the other cells in a pellet at the bottom of the tubes.

In one embodiment, the first and the second centrifugation rounds are performed at a rate below 1500 rounds per minute, 1400 rounds per minute, 1300 rounds per minute, 1200 rounds per minute, 1100 rounds per minute, 1000 rounds per minute, 900 rounds per minute, 800 rounds per minute, 700 rounds per minute, 600 rounds per minute, or 500 rounds per minute.

In one embodiment, the first and the second centrifugation rounds are preferably performed at a different rate.

In one embodiment, the first centrifugation round is performed at a higher rate than the second centrifugation round.

In one embodiment, the first and the second centrifugation rounds are preferably performed for a time ranging from 3 to 20 min.

In one embodiment, the first and the second centrifugation rounds are preferably performed for at least 3 min, 4 min, 5 min, 6 min, 7 min, 8 min, 9 min, 10 min, 11 min, 12 min, 13 min, 14 min, 15 min, 16 min, 17 min, 18 min, 19 min, or 20 min.

After the first round of centrifugation, the sample will show a plurality of layers: a superficial layer of oil and fat tissue, an intermediate yellowish layer and a bottom pellet containing the red blood cells, fibroblasts, smooth muscle cells, and/or white blood cells. The intermediate centrifuged layer comprises the mesenchymal stem cells and will be collected to be subjected to a second centrifugation round.

In one embodiment, the collecting steps are performed as described hereabove.

In one embodiment, the collected intermediate centrifuged layer is resuspended in saline solution before the second centrifugation round.

After the first second of centrifugation, the sample comprises two layers of suspension. The superficial centrifuged layer comprises the stem cells and is collected to be subjected to the purification steps.

In one embodiment, the intermediate centrifuged layer and/or the superficial centrifuged layer comprising mesenchymal stem cells are collected using a pipette. In this embodiment, the pipette is sterile.

In one embodiment, the intermediate centrifuged layer and/or the superficial centrifuged layer comprising mesenchymal stem cells are collected using any means known by the person skilled in the art. In this embodiment, the pipette is sterile.

In one embodiment, the method further comprises changing the osmolarity of the sample before centrifugation. This step comprises adding sterile water to the sample to separate cells from tissue via osmotic shock (or osmotic stress). In this embodiment, said osmotic shock has to be made carefully to avoid the differentiation of the stem cells due to a strong traumatism.

In one embodiment, the method further comprises an optional sonication step before and/or after centrifugation, wherein the sample is subjected to ultrasounds. In this embodiment, ultrasounds has to be dosed carefully to avoid the differentiation of the stem cells due to a strong traumatism.

In one embodiment, the solution resulting the step of flowing a sample of adipose tissue on a polymer surface 1, is collected in a container, a bottle, a tube, or a pouch.

In one embodiment, the solution resulting the step of flowing a sample of adipose tissue on a polymer surface 1, is eliminated after flowing.

In one embodiment, the method further comprises a measuring step to measure the quantity and/or the concentration of mesenchymal stem cells in the suspension of purified mesenchymal stem cells using a flowcytometer as described hereabove. This step will allow a personalized and more efficient use of the resulting suspension of purified mesenchymal stem cells. Indeed, this may lead the user to the decision to take an additional sample to have more cells available and reach a therapeutic threshold.

In one embodiment, the measuring step may be manual, semi-automated, or automated.

While various embodiments have been described and illustrated, the detailed description is not to be construed as being limited hereto. Various modifications can be made to the embodiments by those skilled in the art without departing from the true spirit and scope of the disclosure as defined by the claims.

EXAMPLES

The present invention is further illustrated by the following examples.

Example 1

Adipose tissue is collected by lipoaspiration. The fat tissue is added with an equal volume of saline and an equal volume of non-pyrogenic distilled water and introduced into a vortex heating chamber for 10 minutes at 39° C. The resulting suspension is centrifuged at 1200 rpm for 10 minutes. After the centrifugation round, there are a superficial layer of oil and fat tissue, an intermediate yellowish layer and a bottom pellet containing the red blood cells, fibroblasts, smooth muscle cells, white blood cells. The intermediate centrifuged layer is collected with a sterile pipette and resuspended with saline. A second centrifugation is performed at 700 rpm for 5 minutes. This results in two layers. The superficial layer containing the stem cells is collected and ready for purification. These two centrifugations allow the separation of the stem cells from the other populations.

The resulting suspension is purified using the apparatus 3 of the invention. The suspension is flowed at a first flow rate of 100 ml/mn in the apparatus 3. Then, a rapid flush of 300 ml/mn with saline washes out the almost adherent cells, which are collected at the end of the tubing system. This results in a suspension of purified mesenchymal stem cells.

The same method was performed with a sample of bone marrow, blood umbilical cord, molar, amniotic fluid, follicular tissue (hair), or a sample from a human embryo obtained without the destruction of an embryo.

Example 2

Adipose tissue is collected surgically during a surgical intervention of lipofilling. The fat tissue is added with an equal volume of saline and an equal volume of non pyrogenic distilled water and introduced into a vortex heating chamber for 15 minutes at 39° C. The resulting suspension is centrifuged at 1000 rpm for 14 minutes. After the centrifugation round, there are a superficial layer of oil and fat tissue, an intermediate yellowish layer and a bottom pellet containing the red blood cells, fibroblasts, smooth muscle cells, white blood cells. The intermediate centrifuged layer is collected with a sterile pipette and resuspended with saline. A second centrifugation is performed at 700 rpm for 5 minutes. This results in two layers. The superficial layer containing the stem cells is collected and ready for purification. These two centrifugations allow the separation of the stem cells from the other populations.

The resulting suspension is purified using the apparatus 3 of the invention. The suspension is flowed at a first flow rate of 100 ml/mn in the apparatus 3. Then, a rapid flush of 300 ml/mn with saline washes out the almost adherent cells, which are collected at the end of the tubing system. This results in a suspension of purified mesenchymal stem cells.

The same method was performed with a sample of bone marrow, blood umbilical cord, molar, amniotic fluid, follicular tissue (hair), or a sample from a human embryo obtained without the destruction of an embryo.

Example 3

Adipose tissue is collected surgically during a surgical intervention of debridement of a chronic wound. The fat tissue is added with an equal volume of saline and an equal volume of non pyrogenic distilled water and introduced into a vortex heating chamber for 10 minutes at 39° C. The resulting suspension is centrifuged at 1200 rpm for 10 minutes. After the centrifugation round, there are a superficial layer of oil and fat tissue, an intermediate yellowish layer and a bottom pellet containing the red blood cells, fibroblasts, smooth muscle cells, white blood cells. The intermediate centrifuged layer is collected with a sterile pipette and resuspended with saline. A second centrifugation is performed at 700 rpm for 5 minutes. This results in two layers. The superficial layer containing the stem cells is collected and ready for purification. These two centrifugations allow the separation of the stem cells from the other populations.

The resulting suspension is purified using the apparatus 3 of the invention. The suspension is flowed at a first flow rate of 200 ml/mn in the apparatus 3. Then, a rapid flush of 400 ml/mn with saline washes out the almost adherent cells, which are collected at the end of the tubing system. This results in a suspension of purified mesenchymal stem cells.

The quantity of mesenchymal stem cells in the purified suspension of mesenchymal stem cells is measured using a flowcytometer.

The same method was performed with a sample of bone marrow, blood umbilical cord, molar, amniotic fluid, follicular tissue (hair), or a sample from a human embryo obtained without the destruction of an embryo.

The invention claimed is:

1. A method of purifying adipose-derived mesenchymal stem cells from a sample of adipose tissue comprising mesenchymal stem cells, comprising the steps of:
   flowing said sample comprising mesenchymal stem cells on a polymer surface at a first flow rate allowing to separate said sample into a first remaining sample comprising mesenchymal stem cells on the polymer surface and into a second resulting solution being evacuated from the polymer surface;
   flowing a saline solution on said polymer surface at a second flow rate different from the first flow rate; and
   collecting the saline solution comprising purified mesenchymal stem cells in a collector;
   wherein the first flow rate is slower than the second flow rate;
   wherein the first flow rate is ranging from 10 to 150 ml/min;
   wherein the second flow rate is ranging from 100 to 500 ml/min; and
   wherein the polymer surface comprises at least one vertical helical-shaped portion, at least one vertical threaded shaped portion, or at least one vertical grooved shaped portion.

2. The method according to claim 1, wherein the ratio between the first flow rate and the second flow rate is ranging from 2 to 50.

3. The method according to claim 1, wherein the polymer surface is a polystyrene surface.

4. The method according to claim 1, wherein the polymer surface is the inner surface of a pipe, a tube, a conduit, a duct, a gutter, an open-pipe, or a channel.

5. The method according to claim 4, wherein a portion of the pipe has at least one dimension ranging from 1 mm to 1 cm.

6. An apparatus for implementing the method of purifying adipose-derived mesenchymal stem cells according to claim 1, comprising a polymer surface wherein the polymer surface comprises a geometrical design inducting a minimal flow rate when a control solution is introduced into said polymer surface; wherein the polymer surface comprises at least one vertical helical-shaped portion, at least one vertical threaded shaped portion, or at least one vertical grooved shaped portion.

7. The apparatus for purifying adipose-derived mesenchymal stem cells according to claim 6, wherein the polymer surface is a polystyrene surface.

8. The apparatus for purifying adipose-derived mesenchymal stem cells according to claim 6, further comprising a lumen extending between at least one inlet and at least one outlet, wherein the lumen comprises at least one portion of a polymer surface.

9. The apparatus for purifying adipose-derived mesenchymal stem cells according to claim 6, wherein the polymer surface extends between at least one inlet and at least one outlet, comprises a portion having at least one dimension ranging from 1 mm to 1 cm, and is the surface of a three-dimensional system configured such that as a sample moves forward on said polymer surface, the gravitational potential energy of said sample decreases on at least a portion of said polymer surface.

10. A method for purifying adipose-derived mesenchymal stem cells, comprising flowing a sample of adipose tissue comprising mesenchymal stem cells over the apparatus according to claim 6.

11. A system for implementing the method of purification of adipose-derived mesenchymal stem cells according to claim 1, comprising:
   an apparatus for purifying adipose-derived mesenchymal stem cells, comprising a polymer surface wherein the polymer surface comprises a geometrical design inducting a minimal flow rate when a control solution is introduced into said polymer surface; wherein the polymer surface comprises at least one vertical helical-shaped portion, at least one vertical threaded shaped portion, or at least one vertical grooved shaped portion;
   at least one supplier fluidly connected to the at least one inlet of the apparatus and configured to be fluidly connected to at least one reservoir comprising at least one sample comprising mesenchymal stem cells and to at least one reservoir comprising at least one saline solution;
   at least one collector fluidly connected to the at least one outlet of the apparatus;
   at least one flow controller configured to control the flow rate of a fluid passing through the supplier either at a first flow rate or at a second flow rate; and
   wherein the first flow rate is slower than the second flow rate;
   wherein the first flow rate is ranging from 10 to 150 ml/min; and
   wherein the second flow rate is ranging from 100 to 500 ml/min.

12. The system according to claim 11, wherein the apparatus comprises two inlets and the supplier comprises two tubing; a first tubing configured to fluidly connect the first inlet to at least one sample comprising mesenchymal stem cells and the second tubing configured to fluidly connect the second inlet to at least one saline solution, and wherein the at least one flow controller is configured to flow a fluid passing through the first tubing at a first flow rate and to flow a fluid passing through the second tubing at a second flow rate, wherein the first flow rate is slower than the second flow rate.

13. A method of isolating and purifying adipose-derived mesenchymal stem cells from a sample of adipose tissue, comprising the steps of:
   subjecting the sample to at least one centrifugation round;
   collecting the centrifuged layer comprising mesenchymal stem cells;
   flowing said layer comprising mesenchymal stem cells on a polymer surface at a first flow rate allowing to separate said sample into a first remaining sample comprising mesenchymal stem cells on the polymer surface and into a second resulting solution being evacuated from the polymer surface;
   flowing a saline solution on said polymer surface at a second flow rate; and
   collecting the saline solution comprising purified mesenchymal stem cells in a collector;
   wherein the first flow rate is slower than the second flow rate;
   wherein the first flow rate is ranging from 10 to 150 ml/min;
   wherein the second flow rate is ranging from 100 to 500 ml/min; and
   wherein the polymer surface comprises at least one vertical helical-shaped portion, at least one vertical threaded shaped portion, or at least one vertical grooved shaped portion.

14. The method according to claim 13, wherein the polymer surface is a polystyrene surface.

15. The method according to claim 13, wherein the step of subjecting the sample to at least one centrifugation round comprises the steps of:
- subjecting the sample comprising adipose tissue to a first centrifugation round;
- collecting the intermediate centrifuged layer;
- subjecting said intermediate centrifuged layer to a second centrifugation round; and
- collecting the superficial centrifuged layer comprising mesenchymal stem cells.

* * * * *